US012740520B2

(12) United States Patent
Sánchez Testillano et al.

(10) Patent No.: US 12,740,520 B2
(45) Date of Patent: Sep. 22, 2026

(54) MAMMAL KINASE INHIBITORS TO PROMOTE IN VITRO EMBRYOGENESIS INDUCTION OF PLANTS

(71) Applicant: CONSEJO SUPERIOR DE INVESTIGACIONES CIENTIFICAS (CSIC), Madrid (ES)

(72) Inventors: Pilar Sánchez Testillano, Madrid (ES); Ana Martinez Gil, Madrid (ES); Carmen Gil Ayuso-Gontan, Madrid (ES); Eduardo Berenguer Peinado, Madrid (ES); Elena Carneros García, Madrid (ES); Yolanda Pérez Pérez, Madrid (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 343 days.

(21) Appl. No.: 17/780,331

(22) PCT Filed: Nov. 25, 2020

(86) PCT No.: PCT/EP2020/083316
§ 371 (c)(1),
(2) Date: May 26, 2022

(87) PCT Pub. No.: WO2021/105182
PCT Pub. Date: Jun. 3, 2021

(65) Prior Publication Data

US 2023/0025843 A1 Jan. 26, 2023

(30) Foreign Application Priority Data

Nov. 26, 2019 (EP) .................................... 19383042

(51) Int. Cl.
*A01H 4/00* (2006.01)
*C12N 5/04* (2006.01)

(52) U.S. Cl.
CPC ............... *A01H 4/008* (2013.01); *C12N 5/04* (2013.01)

(58) Field of Classification Search
CPC ................................. A01H 4/008; C12N 5/04
See application file for complete search history.

(56) References Cited

FOREIGN PATENT DOCUMENTS

| | | | | |
|---|---|---|---|---|
| EP | 2484670 A1 | 8/2012 | | |
| WO | 03037072 A2 | 5/2003 | | |
| WO | WO-2016016894 A1 * | 2/2016 | ........... | C12N 5/0606 |
| WO | WO-2018015954 A1 * | 1/2018 | ........... | C12N 5/0606 |
| WO | WO-2019075295 A1 * | 4/2019 | ........... | C12N 15/823 |

OTHER PUBLICATIONS

Testillano et al., "Stress-Induced Microspore Embryogenesis by Anther Culture of *Quercus suber* L.", Springer International Publishing AG, Step Wise Protocols for Somatic Embryogenesis of Important Woody Plants, 2018, vol. 84, pp. 93-105, 13 pages.
Testillano et al., "Somatic Embryogenesis of *Quercus suber* L. From Immature Zygotic Embryos", PubMed, National Library of Medicine, Methods of Molecular Biology, 2018, vol. 1815, pp. 247-256, 10 pages.
Martinez et al., "First Non-ATP Competitive Glycogen Synthase Kinase 3 â (GSK-3â) Inhibitors: Thiadiazolidinones (TDZD) as Potential Drugs for the Treatment of Alzheimer's Disease", PubMed, National Library of Medicine, Journal Medicinal Chemistry, 2002, vol. 45,, Issue 6, pp. 1292-1299, 8 pages.
Kumlehn et al., "Genetic transformation of barley (*Hordeum vulgare* L.) via infection of androgenetic pollen cultures with Agrobacterium tumefaciens", Plant Biotechnology Journal, 2006, vol. 4, pp. 251-261, 11 pages.
Palomo et al., "Subtly Modulating Glycogen Synthase Kinase 3 β: Allosteric Inhibitor Development and Their Potential for the Treatment of Chronic Diseases", PubMed, American Chemical Society, Journal Medicinal Chemistry, 2017, vol. 60, Issue 12, pp. 4983-5001, 19 pages.
Perez et al., "Switching Reversibility to Irreversibility in Glycogen Synthase Kinase 3 Inhibitors: Clues for Specific Design of New Compounds", ACS Publications, Journal Medicinal Chemistry, 2011, vol. 54, Issue 12, pp. 4042-4056, 15 pages.
Prem et al., "A new microspore embryogenesis system under low temperature which mimics zygotic embryogenesis initials, expresses auxin and efficiently regenerates doubled-haploid plants in Brassica napus", BMC Plant Biology, 2012, vol. 12, Article No. 127, 19 pages.
Rodriguez-Serrano et al., "NO, ROS, and cell death associated with caspase-like activity increase in stress-induced microspore embryogenesis of barley", Journal of Experimental Botany, 2012, vol. 63, Issue 5, pp. 2007-2024, 18 pages.
Salado et al, "Leucine rich repeat kinase 2 (LRRK2) inhibitors based on indolinone scaffold: Potential pro-neurogenic agents", Elsevier, European Journal of Medicinal Chemistry, 2017, vol. 138, pp. 328-342, 15 pages.

* cited by examiner

*Primary Examiner* — Bratislav Stankovic
*Assistant Examiner* — George W Meyer
(74) *Attorney, Agent, or Firm* — Bayramoglu Law Offices LLC

(57) ABSTRACT

The present invention relates to the use of mammal kinase inhibitors, preferably human kinase inhibitors, to promote the induction of in vitro embryogenesis, a strategy never used in plants systems before. The results obtained indicated that these inhibitors have beneficial effects in both crop and forest plants in in vitro systems of microspore and somatic embryogenesis.

9 Claims, 10 Drawing Sheets

Specification includes a Sequence Listing.

MAMMAL KINASE INHIBITORS TO PROMOTE IN VITRO EMBRYOGENESIS INDUCTION OF PLANTS

CROSS-REFERENCE TO RELATED APPLICATIONS AND PRIORITY

This patent application claims priority from PCT Application No. PCT/EP2020/083316 filed Nov. 25, 2020, which claims priority from European Patent Application No. 19383042.9 filed Nov. 26, 2019. Each of these patent applications are herein incorporated by reference in their entirety.

The invention relates to the use of mammal kinase inhibitors to promote in vitro induction of plant embryogenesis and plant regeneration. Furthermore, the present invention discloses methods to promote in vitro induction of plant embryogenesis and plant regeneration by the use of mammal kinase inhibitors.

REFERENCE TO AN ELECTRONIC SEQUENCE LISTING

The contents of the electronic sequence listing (SEQ_Listing_Pons_2232.txt; Size: 81, 171 bytes; and Date of Creation: Apr. 15, 2025) is herein incorporated by reference in its entirety.

BACKGROUND ART

The ability of many plant cells to regenerate embryos through in vitro culture is extensively exploited by companies for regeneration, propagation and selection of high quality/adapted plant material in agroforestry and industrial sectors, a technology that permits the propagation of plants with increased genetic gain, reducing time and cost in breeding and conservation programs. The capacity to regenerate adult fertile plants from in vitro cultured explants is well described for many species and through various developmental pathways. Multiple environmental factors have been shown to determine the in vitro responses of plant tissues.

Through in vitro embryogenesis, somatic cells from donor plants can be reprogrammed by different treatments (mainly stress and hormonal treatments), giving rise to entire embryos that further germinate and ultimately produce a plant. In vitro embryogenesis can also be induced from microspores, precursors cells of pollen grains. Due to the haploid condition of these cells, microspore embryogenesis is a useful biotechnological tool in plant breeding as a source of new genetic variability, fixed in fully homozygous plants in only one generation.

In the case of woody species, somatic embryogenesis has many advantages since classical genetic breeding programs have important limitations in trees due to their long-life span, and difficulties of seed conservation and vegetative reproduction. Somatic embryogenesis has a great potential for large-scale propagation and cryopreservation of tree elite genotypes, as well as for transformation strategies.

In vitro systems of somatic and microspore embryogenesis have been developed for many plant species belonging to a wide range of families. The primary advantage of in vitro plant propagation is the rapid production of high numbers of high quality, disease-free and uniform planting material for agroindustry companies. Despite decades of research, poor in vitro regeneration is still a lingering problem with the process still being highly inefficient in many species of economic interest in the fields of agriculture and forestry, a fact that severely affects the application and cost of this technology in plant breeding and conservation programs.

The yield of somatic and microspore-derived embryo production has several bottlenecks at various stages of the process. One of the major problems is the low proportion of cells that are reprogrammed and initiate embryogenesis, being embryogenesis initiation efficiency a crucial step. Therefore, new strategies are necessary to improve in vitro embryogenesis induction in different species of economic interest, such as crops and forest plant species.

DESCRIPTION OF THE INVENTION

To solve the aforementioned limitations, a general object of the invention is to provide the use of mammal kinase inhibitors, preferably human kinase inhibitors, preferably human glycogen synthase kinase-3β (GSK3β) and/or leucine-rich repeat kinase 2 (LRRK2) inhibitors compounds and methods for such uses to induce plant embryogenesis.

In their search for novel strategies to improve the induction of embryogenesis and embryo production of plants, the inventors surprisingly found that mammal kinase inhibitors, preferably human kinase inhibitors, have a positive effect on plant embryogenesis initiation. Moreover, the present disclosure shows that treatments with these inhibitors have been successfully applied to different in vitro protocols, in liquid or solid media, and with direct, indirect and secondary/recurrent embryogenesis, providing similar promoting effects over embryogenesis induction. The inventors have demonstrated that mammal kinase inhibitors, preferably human kinase inhibitors, preferably inhibitors of GSK3β and/or LRRK2 lead to an increase in the in vitro embryogenesis induction, from both somatic cells and microspores, in crop and forest plant species (FIGS. 1-3). Furthermore, the inventors demonstrated that this surprising effect is obtained with several inhibitors for several human kinases, all of them having different molecular structures. (FIGS. 4-5). Additionally, the inventors show that the increase in induction of plant embryogenesis is obtained both in liquid and in solid embryogenesis cultures using as a starting material both microspores (microspore embryogenesis) as well as other plant explants (somatic embryogenesis) (FIGS. 7-12). Moreover, the inventors confirmed through DNA staining and fluorescence microscopy that the proembryos obtained and quantified from cultures treated with the inhibitors were indeed multicellular microspores (FIG. 6), the first sign of embryogenesis initiation. These experiments support the use of such small molecule inhibitors of mammal kinases as new tools to promote the induction and optimization of in vitro plant embryogenesis. Finally, these results suggest that common mechanisms may operate in other in vitro plant systems and that a similar strategy could be extended to other species to increase embryogenesis induction efficiency and plant cell reprogramming.

Thus, a first aspect of the present invention relates to the use of at least a mammal kinases inhibitor to improve in vitro plant embryogenesis induction.

The term "mammal" as used herein refers to any animal classified as a mammal including cows, horses, dogs, cats, rats, mice, primates and human beings. In a preferred embodiment of the invention, the mammal is a human.

The term "kinase" as used herein refers to a member of an enzyme superfamily which functions to phosphorylate one or more proteins, this is, they have protein kinase activity. The terms also relate to a nucleic acid encoding the protein/enzyme.

In a preferred embodiment of the invention the mammal kinases are human kinases.

For the purposes of the invention the mammal kinase, preferably human kinase is selected from a list consisting of: CDK1 (UniProt:P06493), CDK10 (UniProt:Q15131), CDK11A (UniProt:Q9UQ88), CDK11B (UniProt:P21127), CDK12 (UniProt:Q9NYV4), CDK13 (UniProt:Q14004), CDK14 (UniProt:O94921), CDK15 (UniProt:Q96Q40), CDK16 (UniProt:Q00536), CDK17 (UniProt:Q00537), CDK18 (UniProt:Q07002), CDK19 (UniProt:Q9BWU1), CDK2 (UniProt:P24941), CDK20 (UniProt:Q8IZL9), CDK3 (UniProt:Q00526), CDK4 (UniProt:P11802), CDK5 (UniProt:Q00535), CDK6 (UniProt:Q00534), CDK7 (UniProt:P50613), CDK8 (UniProt:P49336), CDK9 (UniProt: P50750), CDKL1 (UniProt:Q00532), CDKL2 (UniProt: Q92772), CDKL3 (UniProt:Q8IVW4), CDKL4 (UniProt: Q5MAI5), CDKL5 (UniProt:O76039), CLK1 (UniProt: P49759), CLK2 (UniProt:P49760), CLK3 (UniProt: P49761), CLK4 (UniProt:Q9HAZ1), DYRK1A (UniProt: Q13627), DYRK1B (UniProt:Q9Y463), DYRK2 (UniProt: Q92630), DYRK3 (UniProt:O43781), DYRK4 (UniProt: Q9NR20), GSK3A (UniProt:P49840), GSK3B (UniProt: P49841), HIPK1 (UniProt:Q86Z02), HIPK2 (UniProt: Q9H2X6), HIPK3 (UniProt:Q9H422), HIPK4 (UniProt: Q8NE63), ICK (UniProt:Q9UPZ9), MAK (UniProt: P20794), MAPK1 (UniProt:P28482), MAPK10 (UniProt: P53779), MAPK11 (UniProt:Q15759), MAPK12 (UniProt: P53778), MAPK13 (UniProt:O15264), MAPK14 (UniProt: Q16539), MAPK15 (UniProt:Q8TD08), MAPK3 (UniProt: P27361), MAPK4 (UniProt:P31152), MAPK6 (UniProt: Q16659), MAPK7 (UniProt:Q13164), MAPK8 (UniProt: P45983), MAPK9 (UniProt:P45984), MOK (UniProt: Q9UQ07), NLK (UniProt:Q9UBE8), PRPF4B (UniProt: Q13523), SRPK1 (UniProt:Q96SB4), SRPK2 (UniProt: P78362), SRPK3 (UniProt:Q9UPE1), ACVR1 (UniProt: Q04771), ACVR1B (UniProt:P36896), ACVR1C (UniProt: Q8NER5), ACVR2A (UniProt:P27037), ACVR2B (UniProt:Q13705), ACVRL1 (UniProt:P37023), AMHR2 (UniProt:Q16671), ANKK1 (UniProt:Q8NFD2), ARAF (UniProt:P10398), BMPR1A (UniProt:P36894), BMPR1B (UniProt:O00238), BMPR2 (UniProt:Q13873), BRAF (UniProt:P15056), ILK (UniProt:Q13418), IRAK1 (UniProt:P51617), IRAK2 (UniProt:O43187), IRAK3 (UniProt: Q9Y616), IRAK4 (UniProt:Q9NWZ3), KSR1 (UniProt: Q8IVT5), KSR2 (UniProt:Q6VAB6), LIMK1 (UniProt: P53667), LIMK2 (UniProt:P53671), LRRK1 (UniProt: Q38SD2), LRRK2 (UniProt:Q5S007), RAF1 (UniProt: P04049), RIPK1 (UniProt:Q13546), RIPK2 (UniProt: O43353), RIPK3 (UniProt:Q9Y572), RIPK4 (UniProt: P57078), TESK1 (UniProt:Q15569), TESK2 (UniProt: Q96S53), TGFBR1 (UniProt:P36897), TGFBR2 (UniProt: P37173), TNNI3K (UniProt:Q59H18), MLKL (UniProt: Q8NB16), —All accession numbers correspond to UniProt release of 16 of October 2019.

In a further embodiment of the present invention, the mammal kinases, preferably human kinases are selected from GSK3β and/or LRRK2.

As used herein the term GSK3β refers to the glycogen synthase kinase 3 beta protein (EC: 2.7.11.26) set forth by Uniprot Accession Nos: P49841-1 (SEQ ID NO: 1) and P49841-2 (SEQ ID NO:2), or alternatively by GenBank Accession Nos. NP_002084.2 (SEQ ID NO: 2), NP_001139628.1 (SEQ ID NO: 1), NP_001341525.1 (SEQ ID NO: 3) and/or XP_006713673.1 (SEQ ID NO: 4) having the WNT signalling regulatory activity via its kinase activity.

In a further embodiment the mammal kinase GSK3β comprises an amino acid sequence with at least 90% identity with any of the SEQ ID NOs.: 1 to 4, preferably 91, 92, 93, 94, 95, 96, 97, 98, 99 or 100% identity with any of the SEQ ID NOs.: 1 to 4. In a more preferred embodiment, the mammal kinase GSK3β comprises any of the SEQ ID NOs.: 1 to 4. In a more preferred embodiment, the mammal kinase GSK3β consists of any of the SEQ ID NOs.: 1 to 4.

The term "identity", as used herein, refers to the proportion of identical amino acids between two compared peptides or proteins or the proportion of identical nucleotides between two compared nucleotide sequences. The methods for comparing sequences are known in the state of the art, and include, but not limited to, the programs BLASTP or BLASTN, ClustalW and FASTA. We can consider that peptides, proteins or nucleotide sequences with percent identities of at least 90% will maintain the same properties as the sequence to which they refer.

As used herein the term LRRK2 refers to the leucine-rich repeat kinase 2 protein (EC 2.7.11.1) set forth by Uniprot Accession No: Q5S007 (SEQ ID NO: 5), or alternatively by GenBank Accession Nos. AAI17181.1 (SEQ ID NO: 6) and/or AAV63975.1 (SEQ ID NO: 7).

In a further preferred embodiment, the mammal kinase LRRK2 comprises an amino acid sequence having at least 90% sequence identity with any of the SEQ ID NO.: 5 to 7, preferably 91, 92, 93, 94, 95, 96, 97, 98, 99 or 100% identity with any of SEQ ID NO.: 5 to 7. In a more preferred embodiment, the mammal kinase LRRK2 comprises any of the SEQ ID NO.: 5 to 7. In a more preferred embodiment, the mammal kinase LRRK2 consists of any of the SEQ ID NO.: 5 to 7.

In a further preferred embodiment of the present invention, the mammal kinase inhibitors to induce in vitro plant embryogenesis are selected from GSK3β inhibitors and/or LRRK2 inhibitors.

As used herein, the term "inhibitor" is interchangeably used to denote "antagonist". These terms define compounds or compositions which have the capability of decreasing certain enzyme activity or competing with the activity or function of a substrate of said enzyme. As used in the present invention, refers to a chemical compound (naturally occurring or non-naturally occurring), such as a biological macromolecule (e.g., polynucleotide, protein or polypeptide, hormone, polysaccharide, lipid), an organic molecule (e.g., a small organic molecule), or an extract made from biological materials such as bacteria, plants, fungi, or animal (particularly mammalian, including human) cells or tissues which has been evaluated to reduce, diminish or inhibit (directly or indirectly) the activity of a kinase.

As used herein the term "GSK3β inhibitor" or "LRRK2 inhibitor" refers to any molecule as described above, capable of inhibiting the activity of GSK3β or LRRK2 as determined by specifically inhibiting levels of phosphorylated substrates specific for GSK3β or LRRK2 (out of total substrates present in a cell).

In a further preferred embodiment of the present invention, the GSK3β inhibitors to induce in vitro plant embryogenesis are selected from a list consisting of thiadiazolidindiones (Formula I), iminothiadiazoles (Formula II), disubstituted maleimides (Formula III) and disubstituted carbohydrazides (Formula IV):

Thiadiazolidindiones of Formula (I):

Formula (I)

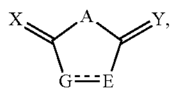

wherein:

A is $-C(R^1)_2-$, $-O-$ or $-NR^1-$;

E is $-NR^1-$ or $-CR^1R^2-$ and the substituent $R^2$ is absent if ------ is a second bond between E and G;

G is $-S-$, $-NR^1-$ or $-CR^1R^2-$ and the substituent $R^2$ is absent if ------ is a second bond between E and G;

------ may be a second bond between E and G where the nature of E and G permits and E with G optionally then forms a fused aryl group;

$R^1$ and $R^2$ are independently selected from hydrogen, $(C_1\text{-}C_8)$alkyl, cycloakyl, haloalkyl, aryl, $-(Z)_n$-aryl, heteroaryl, $-OR^3$, $-C(O)R^3$, $-C(O)OR^3$, $-(Z)_n-C(O)OR^3-$ and $-S(O)_t-$ or as indicated $R^2$ can be such that E with G then form a fused aryl group; Z is independently selected from $-C(R^3)(R^4)-$, $-C(O)-$, $-O-$, $-C(=NR^3)-$, $-S(O)_t-$ and $-N(R^3)-$; n is zero, one or two; t is zero, one or two; $R^3$ and $R^4$ are independently selected from hydrogen, $(C_1\text{-}C_5)$alkyl, aryl and heterocyclic; X and Y are independently selected from $=O$, $=S$, $=N(R^3)$ and $=C(R^1)(R^2)$.

In a preferred embodiment of the inhibitor of Formula (I), A is $-NR^1-$, E is $-NR^1-$, G is $-S-$ and X and Y are from $=O$.

In a more preferred embodiment of the inhibitor of Formula (I), $R^1$ is independently selected from hydrogen, $(C_1\text{-}C_5)$alkyl, aryl, and $-(C(R^3)(R^4))n$-aryl; n is zero, one or two, $R^3$ and $R^4$ are each independently selected from hydrogen, $(C_1\text{-}C_8)$alkyl, aryl and heterocyclic. More preferably $R^1$ is independently selected from $(C_1\text{-}C_8)$alkyl or $-(C(R^3)(R^4))_n$-aryl.

In another preferred embodiment, the inhibitor of Formula (I) is 4-benzyl-2-methyl-1,2,4-thiadozilidine-3,5-dione (TDZD8).

Iminothiadiazoles of Formula (II):

Formula (II)

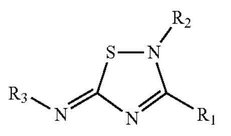

wherein: $R_1$ is selected from H, CN, $NO_2$, F, Cl, Br, I, or a group $X_1-R_1'$ wherein $X_1$ is a single bond or a group selected from $C_1\text{-}C_6$ alkylene, $C_2\text{-}C_6$ alkenylene, $C_2\text{-}C_6$ alkynylene, $C_3\text{-}C_{10}$ cycloalkylene, $C_3\text{-}C_{10}$ heterocycloalkylene, arylene and heteroaryl; being $X_1$ optionally substituted with at least one or more groups which may be identical or different and are selected from H, $C_1\text{-}C_6$ alkyl, $C_2\text{-}C_6$ alkenyl, $C_2\text{-}C_6$ alkynyl, $C_3\text{-}C_{10}$ cycloalkyl, $C_3\text{-}C_{10}$ heterocycloalkyl, F, Cl, Br, I, $-OH$, $=O$, $-CN$, $-NO_2$, $-CO_2R_4$, $-OR_4$, $-SR_4$, $-SO_2NR_4R_5$, $-C(=O)NR_4$ or $-NR_4R_6$;

$R_1'$ is selected from H, $C_1\text{-}C_6$ alkyl, $C_2\text{-}C_6$ alkenyl, $C_2\text{-}C_6$ alkynyl, $C_3\text{-}C_7$ cycloalkyl, $C_1\text{-}C_6$ alkoxy, aryl, heteroaryl, $C_3\text{-}C_{10}$ cycloalkyl or $C_3\text{-}C_{10}$ heterocycloalkyl; being $R_1'$ optionally substituted with one or more groups $X_1'-R_8$ which may be identical or different; being $R_1'$ optionally substituted with one or more groups $X_1'-R_8$ which may be identical or different;

$X_1'$ is a single bond or a group selected from $C_1\text{-}C_6$ alkylene, $C_2\text{-}C_6$ alkenylene, $C_2\text{-}C_5$ alkynylene, arylene, heteroarylene, $C_3\text{-}C_{10}$ cycloalkylene and $C_3\text{-}C_{10}$ heterocycloalkylene, $-C(O)O-$, amino, $-O-$, $-S-$ and $-SO_2-$; being $X_1'$ optionally substituted with at least one or more groups which may be identical or different and are selected from H, $C_1\text{-}C_3$ alkyl, $C_2\text{-}C_5$ alkenyl, $C_2\text{-}C_5$ alkynyl, $C_4\text{-}C_7$ cycloalkyl, F, Cl, Br, I, $=O$, $-CN$, $-NO_2$, $-CO_2R^4$, $-OR^4$, $-SR_4$, $-SO_2NR_6R_7$, $=NR_4$ and $-NR_6R_7$ being $R_6$ and $R_7$ independently selected from $R_4$ and $R_5$ $R_8$ is H, $-OH$, $=O$, $-NO_2$, CN, F, Cl, Br, I, $C_1\text{-}C_4$ alkyl, $-CO_2R_{6a}$, $-C(=O)R_{6a}$, $C(=S)\ R_{6a}$, $SO_2R_{6a}$, $SOR_{6a}$, $SOBR_{6a}$, $SR_{6a}$, $OR_{6a}$, $C(=O)NR_{6a}R_{7a}$, $C(=S)NR_{6a}R_{7a}$, $C(=N-CN)NR_{6a}R_{7a}$, $C(=N-SO_2NH_2)NR_{6a}R_{7a}$, $C(=CH-NO_2)NR_{6a}R_{7a}$, $SO_2NR_{6a}R^{7a}$, $C(=NR_{6a})NHR_{7a}$, $C(=NR_{6a})R_{7a}$ or $NR_{6a}R_{7a}$, being $R_{6a}$ and $R_{7a}$ independently selected from $R_4$ and $R_5$;

$R^4$ and $R^5$ are independently selected from: H, $C_1\text{-}C_6$ alkyl, $C_2\text{-}C_6$ alkenyl, $C_2\text{-}C_6$ alkynyl, $C_3\text{-}C_7$ $X_4$-cycloalkyl, $X_4$-cyclobutyl, $X_4$-cyclopentyl, $X_4$-cyclohexyl, $X_4$-cycloheptyl, $X_4$-benzyl, $X_4$-pyridinyl, $X_4$-pirimidinyl, $X_4$-pyperidinyl, $X_4$-pyrrolidinyl, $X_4$-pyrrolyl, $X_4$-imidazolyl and $X_4$-pyranyl saturated or unsaturated; being optionally substituted the groups $R^4$ and $R^5$ with one or more groups selected from $=O$, $-NO_2$, CN, F, Cl, Br, I, $C_1\text{-}C_4$ alkyl, $-CO_2R_{10}$, $-C(=O)R_{10}$, $C(=S)\ R_{10}$, $SO_2R_{10}$, $SOR_{10}$, $SO_3R_{10}$, $SR_{10}$, $OR_{10}$, $C(=O)NR_{10}R_{11}$, $C(=N-SO_2NH_2)NR_{10}R_{11}$, $C(=CH-NO_2)NR_{10}R_{11}$, $SO_2NR_{10}R_{11}$, $C(=NR_{10})NHR_{11}$, $C(=NR_{10})R_{11}$ and $NR_{10}R_{11}$;

$X_4$ is a single bond or a group selected from $C_1\text{-}C_6$ alkylene, $C_2\text{-}C_6$ alkenylene; each one of the groups optionally substituted with one or more groups which may be identical or different and are selected from $=O$, $-NO_2$, CN, F, Cl, Br, I, $C_1\text{-}C_4$ alkyl, $-CO_2R_{10}$, $-C(=O)R_{10}$, $OR_{10}$, $C(=O)NR_{10}R_{11}$, $-SO_2NR_{10}R_{11}$ and $NR_{10}R_{11}$;

$R_{10}$ and $R_{11}$ are independently selected from H and $C_1\text{-}C_6$ alkyl;

$R_2$ is selected from $C_1\text{-}C_6$ alkyl, $C_2\text{-}C_6$ alkenyl, $C_2\text{-}C_6$ alkynyl, aryl, heteroaryl, $C_3\text{-}C_{10}$ cycloalkyl and $C_3\text{-}C_{10}$ heterocycloalkyl, CN or amino; being $R_2$ optionally substituted with at least one or more groups which may be identical or different and are selected from H, $C_1\text{-}C_6$ alkyl, $C_2\text{-}C_6$ alkenyl, $C_2\text{-}C_6$ alkynyl, aryl, heteroaryl, $C_3\text{-}C_{10}$ cycloalkyl y $C_3\text{-}C_{10}$ heterocycloalkyl, $=O$, $-NO_2$, CN, F, Cl, Br, I, $C_1\text{-}C_4$ alkyl, $-CO_2R_{6b}$, $-C(=O)R_{6b}$, $SO_2R_{6b}$, $SOR_{6b}$, $SO_3R_{6b}$, $SR_{6b}$, $OR_{6b}$, $C(=O)NR_{66}R_{7b}$, $SO_2NR_{6b}R_{7b}$, and $NR_{6b}R_{7b}$, being $R_{6b}$ and $R_{7b}$ independently selected from $R_4$ and $R_5$;

$R_3$ is $-CH_2-R_3'$; $R_3'$ is selected from heteroaryl, $-C(O)OR_{12}$, or $R_3'$ is selected from $-(CH_2)_nOR_{6e}$, n being between 1 and 20, with the condition, that $R_3'$ cannot be $-(CH_2)_2-OH$, $R_{6e}$ being selected from $R_4$ and $R_5$, or $R_3'$ is selected from $-(CH_2)_n-(C_3\text{-}C_{10}$heterocycloalkyl), with n being 0 to 20

$R_{12}$ is independently selected from the groups defined for $R_{10}$;

regarding that "cycloalkyl" comprises preferably a group $C_3\text{-}C_{10}$ cycloalkyl, more particularly a saturated cycloalkyl group saturated with the length indicated in the ring, as for example; cyclopropyl, cyclobutyl, cyclopentyl, cyclohexyl, cycloheptyl, cyclooctyl, cyclononyl, or cyclodecyl and also comprises unsaturated cycloalkyls that contain one or more double bonds in the carbonated chain as for example cycloalkenyl groups $C_3$-$C_{10}$ such as cyclopropenyl, cyclobutenyl, cyclopentenyl, cyclohexenyl, cycloheptenyl, cyclooctenyl, cyclononenyl, or cyclodecenyl and related to the bonds, for the rest of the molecule, the cycloalkyl group may contain single or double bonds, in other words, it may be saturated or unsaturated and may optionally be substituted with one or more times, independently from the other groups with an alkyl group $C_1$-$C_6$ and/or an halogen and/or an OR' group and/or a $NR^{g1}R^{g2}$ group as for example 2-methylcyclopropyl, 2,2-dimethylcyclopropyl, 2,2-dimethylcyclobutyl, 3-hydroxycyclopentyl, 3-hydroxycyclohexyl, 3-dimethylaminocyclobutyl, 3-dimethylaminocyclopentyl and 4-dimethylaminocyclohexyl groups;

and that the term "heterocycloalkyl" comprises preferably a cycloalkyl group $C_3$-$C_{10}$, as defined before, wherein one of the atoms of the rings is an heteroatom like NH, $NR^{d3}$, O, S or groups like C(O), S(O), $S(O)_2$, or also a group $C_n$-cyclo alkyl, wherein n is a number selected from 3, 4, 5, 6, 7, 8, 9 and 10, wherein one or more of the carbon atoms are substituted by the heteroatoms or before cited groups in order to be a $C_n$-cycloheteroalkyl group; they also comprises unsaturated cycloheteroalkyl groups that contain one or more double bonds in the carbonated chain, therefore related to the bonds, for the rest of the molecule, cycloheteroalkyl group may contain single and double bonds, in other words, it may be saturated or unsaturated and may optionally substituted one or more times, independently of the other groups with an alkyl group $C_1$-$C_6$ and/or an halogen and/or an OR' group and/or a group and that the $C_n$-cycloheteroalkyl group is related for example to heterocycles of three members expressed as $C_3$-heterocycloalkyl named oxyranyles.

In a preferred embodiment, the inhibitor of Formula of formula (II) is selected from:

2,3-Diphenyl-5-(3-pyridylmethylimino)-2,5-dihydro-1,2,4-thiadiazole 3-(4-Methoxyphenyl)-2-phenyl-5-(3-pyridylmethylimino)-2,5-dihydro-1,2,4-thiadiazole 2-(4-Methoxyphenyl)-3-phenyl-5-(3-pyridylmethylimino)-2,5-dihydro-1,2,4-thiadiazole 2-(4-Nitrophenyl)-3-phenyl-5-(3-pyridylmethylimino)-2,5-dihydro-1,2,4-thiadiazole 2-Phenyl-5-(3-pyridylmethylimino)-3-(4-trifluoromethylphenyl)-2,5-dihydro-1,2,4-thiadiazole 2-(1-Naphthyl)-3-phenyl-5-(3-pyridylmethylimino)-2,5-dihydro-1,2,4-thiadiazole 3-(1-Naphthyl)-2-phenyl-5-(3-pyridylmethylimino)-2,5-dihydro-1,2,4-thiadiazole 3-Methyl-2-phenyl-5-(3-pyridylmethylimino)-2,5-dihydro-1,2,4-thiadiazole 5-Ethoxycarbonylmethylimino-2,3-diphenyl-2,5-dihydro-1,2,4-thiadiazole 5-Ethoxycarbonylmethylimino-3-(4-methoxyphenyl)-2-phenyl-2,5-dihydro-1,2,4-thiadiazole 5-Ethoxycarbonylmethylimino-2-(4-methoxyphenyl)-3-phenyl-2,5-dihydro-1,2,4-thiadiazole 5-Ethoxycarbonylmethylimino-2-(4-nitrophenyl)-3-phenyl-2,5-dihydro-1,2,4-thiadiazole 5-(2-Hydroxyethylimino)-2,3-diphenyl-2,5-dihydro-1,2,4-thiadiazole 5-(2-Hydroxyethylimino)-3-(4-methoxyphenyl)-2-phenyl-2,5-dihydro-1,2,4-thiadiazole 5-(2-Hydroxyethylimino)-2-(4-methoxyphenyl)-3-phenyl-2,5-dihydro-1,2,4-thiadiazole 5-(2-Hydroxyethylimino)-2-(1-naphthyl)-3-phenyl-2,5-dihydro-1,2,4-thiadiazole 5-(2-Hydroxyethylimino)-3-(1-naphthyl)-2-phenyl-2,5-dihydro-1,2,4-thiadiazole, and 5-(2-Morpholinethylimino)-2,3-diphenyl-2,5-dihydro-1,2,4-thiadiazole.

More preferably 5-(2-Morpholinethylimino)-2,3-diphenyl-2,5-dihydro-1,2,4-thiadiazole (VP3.15).

Disubstituted Maleimides of Formula (III):

Formula (III)

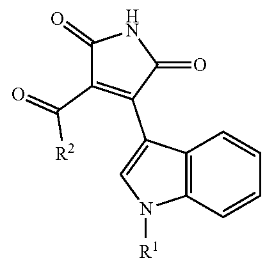

wherein: $R^1$ is selected from H or $C_1$-$C_{10}$ alkyl and $R^2$ is selected from $C_1$-$C_{10}$ alkyl or $C_2$-$C_{10}$ alkenyl; being optionally substituted by halogen.

In a preferred embodiment of the inhibitor of Formula (III), $R^1$ is $C_1$-$C_5$ alkyl and $R^2$ is $C_1$-$C_5$ alkyl.

In a more preferred embodiment, the inhibitor of Formula (III) is 3-acetyl-4-(1-methyl-1H-indol-3-yl)-1H-pirrol-2,5-dione (VP3.36).

Disubstituted Carbohydrazides of Formula (IV):

Formula (IV)

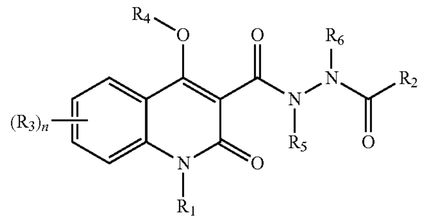

wherein $R_1$ is selected from H and $C_1$-$C_5$ alkyl, optionally substituted, $R_2$ is $C_5$-$C_{15}$ alkyl, optionally substituted, $R_3$ is selected from H, halogen, $C_1$-$C_5$ alkyl, optionally substituted, and —(O)—$C_1$-$C_5$ alkyl, optionally substituted, n is between 1 and 4, $R_4$, $R_5$ y $R_6$ are each independently selected from H and $C_1$-$C_5$ alkyl, optionally substituted.

In a preferred embodiment of the inhibitor of Formula (IV), $R_3$, $R_4$, $R_5$, or $R_6$ are H.

In another preferred embodiment of the inhibitor of Formula (IV), $R_1$ and $R_2$ are each independently selected from $C_9$-$C_{12}$ alkyl.

In a more preferred embodiment, the inhibitor of Formula (IV) is 4-hydroxy-1-ethyl-N'-palmitoyl-2-oxo-1,2-dihydroquinoline-3-carbohydrazide (VP0.7).

For the purposes of the current invention, preferably the GSK3β inhibitors are selected from: 4-benzyl-2-methyl-1,2,4-thiadozilidine-3,5-dione (TDZD8); 5-(2-morpholinethylimino)-2,3-diphenyl-2,5-di-hydro-1,2,4-thiadiazole (VP3.15); 3-acetyl-4-(1-methyl-1H-indol-3-yl)-1H-pirrol-2,5-dione (VP3.36); and 4-hydroxy-1-ethyl-N'-palmitoyl-2-oxo-1,2-dihydroquinoline-3-carbohydrazide (VP0.7).

In a further embodiment of the present invention, the LRRK2 inhibitors to induce in vitro plant embryogenesis are selected from the substituted N-(benzotiazolil-4-morfolino-benzamide (Formula V) and the (E,Z)-3-(morpholinoimino) indolin-2-one, named as IGS4.75.

Formula (V)

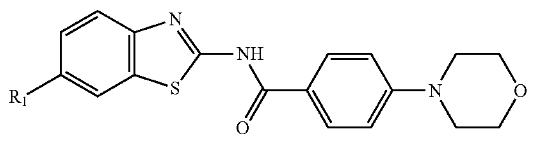

wherein: $R_1$ is selected from H, $C_1$-$C_6$ alkyl, halogen, $CF_3$, and —O—$C_1$-$C_6$·alkyl.

In a preferred embodiment of the inhibitor of Formula (V), $R_1$ is H.

In another preferred embodiment of the inhibitor of Formula (V), $R_1$ is a $C_1$-$C_4$ alkyl. In a more preferred embodiment of the compound (V), $R_1$ is selected from methyl or isopropyl.

In another preferred embodiment of the inhibitor of Formula (V), $R_1$ is selected from F, Cl or Br.

In another preferred embodiment of the inhibitor of Formula (V), $R_1$ is a —O—$C_1$-$C_4$ alkyl. In a more preferred embodiment of the inhibitor of Formula (V), $R_1$ is selected from —O-methyl, —O-ethyl and —O-propyl.

In another preferred embodiment of the inhibitor of Formula (V), $R_1$ is $CF_3$.

In another preferred embodiment, the inhibitor of Formula (V) is selected from the following list:

N-(benzothiazole-2-yl)-4-morpholinobenzamide,
N-(6-methoxybenzothiazole-2-yl)-4-morpholinobenzamide,
N-(6-trifluoromethylbenzothiazole-2-yl)-4-morpholinobenzamide,
N-(6-methylbenzothiazole-2-yl)-4-morpholinobenzamide (JZ1.3),
N-(6-chlorobenzothiazole-2-yl)-4-morpholinobenzamide,
N-(6-fluorobenzothiazole-2-yl)-4-morpholinobenzamide (JZ1.6),
N-(6-ethoxybenzothiazole-2-yl)-4-morpholinobenzamide,
N-(6-bromobenzothiazole-2-yl)-4-morpholinobenzamide (JZ1.24),
N-(6-propoxybenzothiazole-2-yl)-4-morpholinobenzamide,
N-(6-isopropylbenzothiazole-2-yl)-4-morpholinobenzamide.

More preferably the inhibitor of Formula (V) is selected from N-(6-methylbenzothiazole-2-yl)-4-morpholinobenzamide (JZ1.3), N-(6-fluorobenzothiazole-2-yl)-4-morpholinobenzamide, (JZ1.6) and N-(6-bromobenzothiazole-2-yl)-4-morpholinobenzamide (JZ1.24).

For the purposes of the current invention, preferably the LRRK2 inhibitors are selected from: N-(6-metilbenzotiazol-2-il)-4-morfolinobenzamida (JZ1.3), N-(6-flurobenzotiazol-2-il)-4-morfolinobenzamida, (JZ1.6) and N-(6-bromobenzotiazol-2-il)-4-morfolinobenzamida (JZ1.24) and (E,Z)-3-(morpholinoimino) indolin-2-one (IGS4.75).

In another embodiment of the present invention, the induction of in vitro plant embryogenesis comprises increased plant embryo growth and/or increased embryo production yield. As it is shown in the examples, the results states that all of the inhibitors tested lead to an increase of embryogenesis induction efficiency in the range of 20-25% for GSK3β inhibitors and 23-30% for LRRK2 inhibitors, when applied at their optimal concentration.

As used herein, the term "plant embryo growth regulator" refers to any compound capable of inducing plant embryo growth, preferably embryos from agricultural and/or forest plant.

As used herein, the term "embryo production yield" refers to the number of individual embryos resulting from in vitro embryogenesis induction, preferably microspore and/or somatic embryogenesis.

In another embodiment of the present invention, the mammal kinase inhibitors are used in in vitro plant embryogenesis wherein the embryogenesis is somatic and/or by microspores.

The term "somatic embryogenesis" as used herein refers to a type of plant tissue culture where a piece of a donor plant, composed by somatic cells, is excised, cultured and induced to form multiple embryos, which can further germinate and produce entire plants.

The term "microspore embryogenesis" as used herein refers to a unique process in which haploid, immature pollen (microspores) are induced by different treatments to form embryos in culture. These microspore-derived embryos can then be germinated and converted to homozygous doubled haploid plants by chromosome doubling agents and/or through spontaneous doubling.

In a further embodiment of the present invention, the mammal kinase inhibitors are used to induce in vitro plant embryogenesis wherein the plants are crops and/or forests plants.

As used herein the term "plant" refers to a whole plant or parts thereof. The phrase "plant part" refers to isolated plant cells or isolated plant parts (tissues) such as from which plants can be (re) generated, including plant protoplasts, plant cali, plant clumps, and plant cells that are intact in plants, or part of plants, such as seeds, leaves, stems, pollens, roots, root tips, anthers, ovules, petals, flowers, seedlings, embryos and bolls.

In a preferred embodiment the crop plants as used herein are selected from the list consisting of: *Medicago* spp., *Prunus* spp., *Angelica* spp., *Pimpinella* spp., *Ceratonia siliqua, Malus* spp., *Areca* spp, *Arracacia* spp, *Maranta* spp., *Cynara* spp., *Daucus carota, Anacardium occidentale, Asparagus* spp., *Persea* spp., Pearl spp., *Pennisetum* spp., *Vigna* spp., *Musa* spp., *Sechium edule, Jatropha* spp., *Cocos nucifera, Hordeum* spp., *Apium graveolens, Cyclamen* spp., *Atalantia* spp. *Anethum graveolens, Vigna subterranea, Laurus* spp., *Phaseolus* spp. *Ocimum* spp., *Cinnamomum verum, Paulinia cupana, Areca* spp., *Annona reticulate, Piper* spp., *Acacia* spp., *Rubus* spp. *Vaccinium* spp. *Bertholletia excelsa, Sesamum indicum, Artocarpus* spp., *Vicia* spp, *Fagopyrum esculentum, Carum carvi, Elettaria cardamomum, Ricinus communis, Castanea sativa, Cicer* spp. *Cichorium* spp, *Eugenia aromatica, Syzygium aromaticum, Trifolium* spp. *Erythroxylum* spp., *Cola* spp., *Brassica* spp., *Valerianella locusta, Gossypium* spp., *Lepidium sativum, Cucumis* spp., *Ficus carica, Corylus* spp., *Furcraea macrophylla, Linum* spp., *Geranium* spp., *Zingiber* spp., *Panax* spp., *Ribes* spp., *Vitis vinifera, Lygeum spartum, Dactylis* spp., *Arachis hypogaea, Corylus avellana, Cannabis sativa, Crotalaria juncea, Lawsonia inermis, Armoracia rusticana, Indigofera tinctoria, Jasminum* spp., *Helianthus* spp., *Actinidia deliciosa, Lavandula* spp., *Citrus* spp., *Cymbopogon citratus, Lens culinaris, Lespedeza* spp., *Lactuca* spp., *Litchi chinensis, Eriobotrya japonica, Lupinus* spp., *Macadamia* spp., *Zea mays, Mangifera* spp., *Secale* spp, *Setaria italica, Echinochloa esculenta, Pennisetum americanum, Panicum miliaceum, Mentha* spp., *Morus* spp., *Sinapis* spp., *Avena* spp., *Elaeis guineensis, Abelmoschus esculentus, Hibiscus esculentus, Olea* spp, *Allium* spp., *Papaver* spp., *Borassus flabellifer, Elaeis guineensis, Pastinaca sativa, Pisum sativum, Pyrus communis, Carya illinoensis, Capsicum* spp., *Cajanus cajan, Ananas comosus, Pistacia vera, Punica granatum, Solanum* spp., *Ipomoea* spp. *Cucurbita* spp., *Chrysanthemum* spp., *Aspidosperma* spp., *Cydonia oblonga, Cinchona* spp., *Chenopodium quinoa, Raphanus sativus, Rubus* spp., *Agrostis* spp., *Rheum* spp., *Oryza* spp., Rose spp., *Hevea brasiliensis, Lolium* spp. *Crocus sativus, Vitellaria paradoxa, Butyrospermum parkii, Agave* spp., *Glycine* spp., *Triticum* spp., *Spinacia oleracea, Fragaria* spp., *Beta* spp., *Sorghum* spp., *Thymus* spp., Timothy spp., *Phleum pratense, Phleum alpinum, Saccharum officinarum, Nicotiana* spp., *Bixa* spp, *Solanum* spp., *Lotus* spp., *Triticale* (Hybrid of *Triticum aestivum* and *Secale cereale*), *Curcuma* spp., *Vanilla planifolia, Juglans* spp., *Citrullus lanatus, Dioscorea* spp., *Ilex paraguariensis, Pennisetum glaucum, Setaria italic, Eleusine coracana, Panicum virgatum, Echinochloa frumentacea, Paspalum scrobiculatum, Digitaria exilis, Milium effusum, Phalaris canariensis, Coix lacryma-jobi*. Where so applicable the crop plants species here listed include all different subspecies, varieties and cultivars existent, including, without limitation, regional, seasonal and agricultural varieties.

In a more preferred embodiment, the crop plants are selected from the list consisting of: *Hordeum* spp., *Zea mays, Secale* spp, *Setaria italica, Panicum miliaceum, Avena* spp., *Oryza* spp., *Triticum* spp, *Sorghum* spp., *Triticale* (Hybrid of *Triticum aestivum* and *Secale cereale*), *Pennisetum glaucum, Eleusine coracana, Phalaris canariensis, Cynara* spp., *Daucus carota, Piper* spp, *Trifolium* spp, *Brassica* spp, *Lactuca* spp, *Mentha* spp, *Allium* spp., *Pisum sativum, Capsicum* spp, *Solanum* spp, *Cucurbita* spp, *Chenopodium quinoa, Rubus* spp, *Spinacia oleracea, Beta* spp, *Solanum* spp., *Helianthus* spp., *Gossypium* spp, *Arachis hypogaea, Cannabis sativa, Saccharum officinarum, Linum* spp., *Glycine* spp., *Nicotiana* spp, *Medicago* spp., and/or *Agrostis* spp. In a more preferred embodiment, the crop plants belong to *Hordeum* spp, and/or *Brassica* spp.

In another preferred embodiments the forest plants are selected from a list consisting of: *Araucaria* spp., *Cryptomeria japonica, Cupressus* spp, *Juniperus* spp., *Sequoia sempervirens, Sequoiadendron giganteum, Thuja* spp, *Abies* spp., *Cedrus* spp, *Larix* spp, *Picea* spp., *Pinus* spp., *Pseudotsuga* spp, *Taxus* spp., *Ginkgo biloba, Acer* spp., *Anacardium occidentale, Mangifera* spp, *Pistacia* spp, *Cocos nucifera, Phoenix* spp, *Betula* spp., *Corylus* spp, *Paulownia tomentosa, Adansonia* spp, *Capparis* spp, *Sambucus* spp., *Carica papaya, Euonymus* spp, Hevea *brasiliensis, Manihot* spp., *Acacia* spp., *Robinia* spp, *Castanea* spp, *Fagus* spp, *Quercus* spp., *Carya* spp., *Juglans* spp., *Cinnamomum* spp., *Laurus* spp, *Persea* spp., *Swietenia* spp., *Artocarpus* spp., *Ficus* spp., *Morus* spp., *Myrtus communis, Psidium* spp., *Nothofagus* spp., *Fraxinus* spp., *Olea europaea, Platanus* spp, *Dendrocalamus asper, Malus* spp., *Photinia* spp, *Photinia* x *fraser, Prunus* spp., *Pyrus* spp., *Coffea* spp., *Citrus* spp., *Populus* spp., *Salix* spp., *Solanum erianthum; Theobroma cacao, Camellia* spp., *Tilia* spp., *Ulmus* spp., Tamarillo, (*Cyphomandra betacea* (Cav.) (Sendtn.); *Solanum betaceum* Cav.), Indian olive (*Elaeocarpus robustus* L.); bottle palm (*Hyophorbe lagenicaulis*), Indian rosewood (*Dalbergia sissoo*), canela petrea (*Ocotea catharinensis* Mez.), Sandalwood (*Santalum album*), *Echinacea purpurea* L., longan (*Dimocarpus longan* Lour.), (*Aspidosperma polyneuron* Mull.Arg), rattan (*Calamus* spp.), jojoba (*Simmondsia chiensis*), (*Aegle marmelos* L.), black cohosh (*Actaea racemosa* L.), *Gomortega keule, Cyclamen* spp., Hybrid Aspen (*Populus tremuloides* x *Populus tremula*), Oil palm (*Elaeis guineensis* Jacq.), *Passiflora* spp., Açaí palm (*Euterpe oleracea* Mart.), tree-fern (*Cyathea delgadii* Sternb.), *Eucalyptus* spp., Hybrid Larch (*Larix* x *eurolepis* Henry), neem (*Azadirachta indica*). Where so applicable the forest plants species here listed include all different sub-species, varieties and cultivars existent, including, without limitation, regional, seasonal and agricultural varieties.

In a more preferred embodiment, the forest plants are selected from the list consisting of: *Araucaria* spp., *Cupressus* spp, *Juniperus* spp., *Abies* spp., *Cedrus* spp, *Larix* spp, *Picea* spp., *Pinus* spp., *Pseudotsuga* spp, *Taxus* spp., *Ginkgo biloba, Acer* spp., *Anacardium occidentale, Mangifera* spp, *Pistacia* spp, *Cocos nucifera, Phoenix* spp, *Betula* spp., *Corylus* spp, *Carica papaya, Hevea brasiliensis, Acacia* spp., *Robinia* spp, *Castanea* spp, *Fagus* spp, *Quercus* spp., *Cinnamomum* spp., *Laurus* spp, *Persea* spp., *Morus* spp., *Psidium* spp., *Fraxinus* spp., *Olea europaea, Platanus* spp, *Malus* spp., *Prunus* spp., *Pyrus* spp., *Coffea* spp., *Citrus* spp., *Populus* spp., *Salix* spp., *Theobroma cacao, Camellia* spp., *Ulmus* spp., Tamarillo, (*Cyphomandra betacea* (Cav.) (Sendtn.); *Eucalyptus* spp. In a more preferred embodiment, the forest plants belong to *Quercus* spp.

In a further aspect, the invention relates to a method, here onwards the method of the invention, to induce in vitro plant embryogenesis, where the method comprising:

a. culturing the microspores and/or explants in a culture medium suitable for embryo development; and
b. adding mammal kinase inhibitors to the culture medium of step a); and
c. culturing for a period sufficient to obtain embryos.

The term "culture medium" as used herein is intended to indicate any material either solid or liquid in which plant cells, tissues, organs and whole plants may grow. Additives may be provided to the cells in the form of media, and environmental conditions controlled. There are many types of plant tissue culture media comprised of mixtures of mineral salts containing essential oligoelements plus various additives like amino acids, sugars, growth regulators and vitamins which must therefore be added to the culture medium to allow development of (pro) embryo, explant and/or plant growth. Examples of plant tissue culture medium are, without limitation, Chu (N6) medium (Duchefa, Sigma-Aldrich), Clc/Ipomoea CP medium (Duchefa), CLC/Ipomoea ep medium (Duchefa), DKV/Junglans medum (Duchefa, Sigma-Aldrich), Erikson medium (Duchefa), Gamborg B5 medium (Duchefa, Sigma-Aldrich), Gresshoff and Doy medium (Duchefa), Lindemann orchid medium (Duchefa), NLN medium (Duchefa), Nitsch medium (Duchefa), Woody plant medium (Duchefa, Sigma-Aldrich), Linsmaier and Skoog medium (Duchefa), Litvay medium (Duchefa), Quorin and Lepoivre medium (Duchefa), Rugini olive medium (Duchefa), Schenk and Hildebrant medium (Duchefa, Sigma-Aldrich), White's medium (Duchefa, Sigma-Aldrich), Westvaco WV5 medium (Duchefa), Murashige and Skoog medium (Duchefa, Sigma-Aldrich), Murashige and Skoog medium with B5 vitamins (Duchefa), Murashige and Skoog medium with Nitsch vitamins (Duchefa), Murashige and Skoog medium van der Salm (Duchefa), Hoagland's no. 2 basal salt mixture (Sigma-Aldrich), Sommer macronutrients+MS micronutrients and vitamins (Testillano et al. 2018, Plant Cell Culture Protocols, eds. V. M. Loyola-Vargas & N. Ochoa-Alejo. Springer and Bussines Media. pp. 247-256), KBP medium (Kumlehn et al. 2006).

As used herein, the term "plant embryo" refers to a somatic plant embryo or a microspore plant embryo. Somatic plant embryos may be produced by culturing embryogenic tissue by standard methods under laboratory conditions in which some of the cells comprising the tissue, the responsive ones, are induced to reprogram and develop into complete embryos. In the same sense, microspore plant embryo may be produced by culturing either anthers containing microspores or isolated microspores in appropriate culture medium under defined conditions in which some microspores, the responsive ones, are induced to reprogram and develop into complete haploid and doubled-haploid embryos.

As used herein, "plant embryo" includes embryos at various stages of development.

The term "explant" as used herein refers to a piece of tissue taken from a donor plant for culturing.

In a preferred embodiment, the method of the invention is a method wherein the embryogenesis is somatic and/or by microspores.

All the terms and definitions mentioned previously by the use of the mammal's kinase inhibitors to induce in vitro plant embryogenesis, apply in the same way to the method to induce in vitro plant embryogenesis disclosed herein.

Thus, in another preferred embodiment, the method of the invention is a method wherein the mammal kinases are human kinases, preferably GSK3β and/or LRRK2, as it has been disclosed previously.

In a further preferred embodiment, the method of the invention is a method wherein the plants are crops and/or forest plants.

In yet another preferred embodiment, the method of the invention is a method wherein the crop plants are selected from the list consisting of: *Hordeum* spp., *Zea mays, Secale* spp, *Setaria italica, Panicum miliaceum, Avena* spp., *Oryza* spp., *Triticum* spp, *Sorghum* spp., *Triticale* (Hybrid of *Triticum aestivum* and *Secale cereale*), *Pennisetum glaucum, Eleusine coracana, Phalaris canariensis, Cynara* spp., *Daucus carota, Piper* spp, *Trifolium* spp, *Brassica* spp, *Lactuca* spp, *Mentha* spp, *Allium* spp., *Pisum sativum, Capsicum* spp, *Solanum* spp, *Cucurbita* spp, *Chenopodium quinoa, Rubus* spp, *Spinacia oleracea, Beta* spp, *Solanum* spp., *Helianthus* spp., *Gossypium* spp, *Arachis hypogaea, Cannabis sativa, Saccharum officinarum, Linum* spp., *Glycine* spp., *Nicotiana* spp, *Medicago* spp., and/or *Agrostis* spp. In a more preferred embodiment, the crop plants belong to *Brassica* spp, and/or *Hordeum* spp.

In another preferred embodiment, the method of the invention is a method wherein the forest plants are selected from the list consisting of: *Araucaria* spp., *Cupressus* spp, *Juniperus* spp., *Abies* spp., *Cedrus* spp, *Larix* spp, *Picea* spp., *Pinus* spp., *Pseudotsuga* spp, *Taxus* spp., *Ginkgo biloba, Acer* spp., *Anacardium occidentale, Mangifera* spp, *Pistacia* spp, *Cocos nucifera, Phoenix* spp, *Betula* spp., *Corylus* spp, *Carica papaya, Hevea brasiliensis, Acacia* spp., *Robinia* spp, *Castanea* spp, *Fagus* spp, *Quercus* spp., *Cinnamomum* spp., *Laurus* spp, *Persea* spp., *Morus* spp., *Psidium* spp., *Fraxinus* spp., *Olea europaea, Platanus* spp, Malus spp., *Prunus* spp., *Pyrus* spp., *Coffea* spp., *Citrus* spp., *Populus* spp., *Salix* spp., *Theobroma cacao, Camellia* spp., *Ulmus* spp., *Tamarillo*, (*Cyphomandra betacea* (Cav.) (Sendtn.); *Eucalyptus* spp. In a more preferred embodiment, the forest plants belong to *Quercus* spp.

In a further preferred embodiment, the method of the invention is a method wherein the GSK3β inhibitors used are the same as described above. In a more preferred embodiment, the GSK3β inhibitors are selected from a list consisting of: 4-benzyl-2-methyl-1,2,4-thiadozilidine-3,5-dione (TDZD8), 5-(2-Morpholinethylimino)-2,3-diphenyl-2,5-dihydro-1,2,4-thiadiazole (VP3.15), 3-acetyl-4-(1-methyl-1H-indol-3-yl)-1H-pirrol-2,5-dione (VP3.36), 4-hydroxy-1-ethyl-N'-palmitoyl-2-oxo-1,2-dihydroquinoline-3-carbohydrazide (VP0.7).

In a further preferred embodiment, the method of the invention is a method wherein the LRRK2 inhibitors used are the same as described above. In a more preferred embodiment, are selected from a list consisting of: N-(6-metilbenzotiazol-2-il)-4-morfolinobenzamida (JZ1.3), N-(6-flurobenzotiazol-2-il)-4-morfolinobenzamida (JZ1.6), N-(6-bromobenzotiazol-2-il)-4-morfolinobenzamida (JZ1.24), and (E,Z)-3-(morpholinoimino) indolin-2-one (IGS4.75).

In a further preferred embodiment, the method of the invention is a method wherein the inhibitor concentration ranges from 0.1 μM to 100 μM inclusive. Preferably the inhibitor concentrations have ranges of 0.5-10 μM, 10-20 μM, 20-30 μM, 30-40 μM, 40-50 μM, 50-60 μM, 70-80 μM, 80-90 μM, 90-100 μM. More preferably the inhibitor concentrations have ranges of 0.1-5 μM, 5-10 μM, 10-15 μM, 15-20 μM, 20-25 μM, 25-30 μM, 30-35 μM, 35-40 μM, 40-45 μM, 45-50 μM, 50-55 μM, 55-60 μM, 60-65 μM, 65-70 μM, 70-75 μM, 75-80 μM, 80-85 μM, 85-90 μM, 90-95 μM, 95-100 μM.

In a further preferred embodiment, the method of the invention is a method wherein the culture medium is a liquid medium and the inhibitor concentration ranges from 0.1 μM to 100 μM inclusive, preferably from 0.5 μM to 5 μM inclusive.

In another preferred embodiment, the method of the invention is a method wherein the culture medium is a solid medium and the inhibitor concentration ranges from 0.1 μM to 100 μM inclusive, preferably from 25 μM to 100 μM, preferably from 25 μM to 50 μM.

In a more preferred embodiment, wherein the embryogenesis is an embryogenesis from microspores, the inhibitor concentration ranges from 0.1 μM to 100 μM inclusive, preferably from 0.5 μM to 10 μM and more preferably from 0.5 μM to 5 μM wherein the culture medium is a liquid media. In another preferred embodiment, the inhibitor concentration ranges from 20 μM to 100 μM inclusive, preferably from 25 μM to 50 μM, wherein the culture medium is a solid media.

In a more preferred embodiment, wherein the embryogenesis in a somatic embryogenesis, the inhibitor concentration ranges from 20 μM to 100 μM inclusive, preferably from 25 μM to 50 μM, wherein the culture medium is a solid media.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

EXAMPLES

Methodology 1.1. Microspore Embryogenesis of *B. napus*, Through Isolated Microspore Culture (Protocol without Inhibitors)

*B. napus* L. (rapeseed) cv. 'Topas' line DH407 plants were used as donor plants. Rapeseed seeds were germinated and grew under controlled conditions (relative humidity 60%, 15° C. under long-day photoperiod 16 h light and 8 h dark at 10° C.) in a growth chamber in pots containing a mixture of organic substrate and vermiculite (2/1, v/v).

Figure 1:
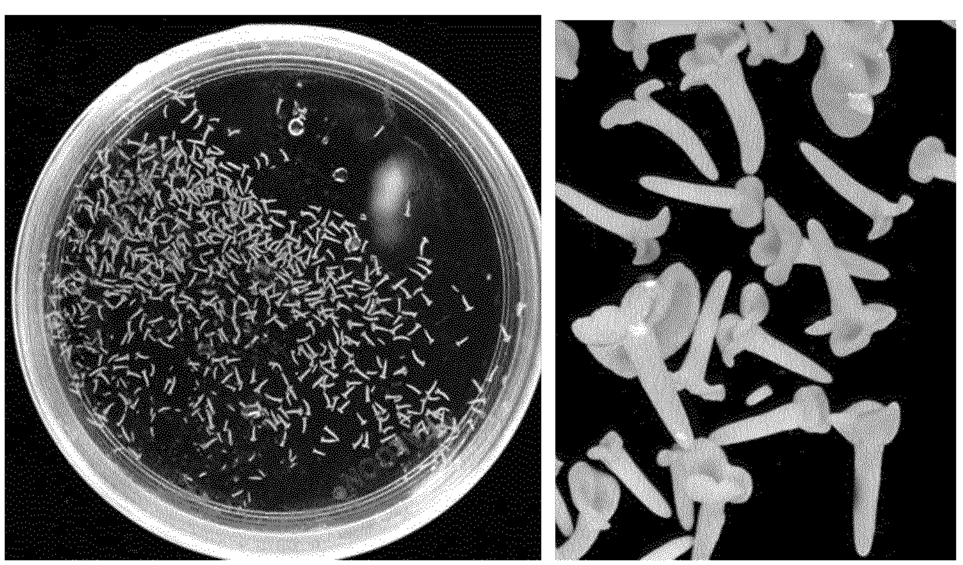
FIG. 1. In vitro microspore embryogenesis in *B. napus*. Cotyledonary embryos developed from isolated microspore culture in liquid medium without mammal's kinase inhibitors.

Flower buds containing vacuolated microspores, the most responsive stage for microspore induction, were isolated for microspore culture as previously described (Prem et al., 2012 BMC Plant Biology 12, 127). The selected buds were surface-sterilized in 5.0% (v/v) commercial bleach (5% active chlorine) for 20 min and then rinsed 6-7 times with sterile distilled water. Ten to 15 buds were crushed using a cold mortar and pestle in 5 ml of cold NLN-13 medium containing 13% sucrose (w/v). The suspension was filtered through 48 μm nylon mesh and the filtrate collected in 15-ml falcon centrifuge tubes. The crushed buds were rinsed with 5 ml NLN-13 to make up the volume to 10 ml and the filtrate was then centrifuged at 1100 rpm for 5 min at 4° C. The pellet was re-suspended in 10 ml of cold NLN-13 and centrifuged as mentioned above. This process was repeated three times for washing of the microspores. The final pellet was suspended in the NLN-13, and the cell density was adjusted to 10,000 cells per ml. The cell suspension was then poured into 90-mm Petri dishes (10 ml per Petri dish) and cultured in darkness. For embryogenesis induction, microspore cultures were subjected to an in vitro stress treatment of 32° C. for 15 days. In response to the inductive treatment, responsive microspores divide and produce multicellular structures or proembryos, still confined within the microspore wall (exine). Such structures are considered to be the first sign of embryogenesis initiation; they can be found after 4-6 days in culture. When globular/heart shaped embryos were observed (around 20 days), cultures were shifted to 25° C. on a gyratory shaker at 60 rpm until complete development and maturation of the embryos was observed (FIG. 1), normally around 30 days in culture.

1.2. Microspore Embryogenesis of *H. vulgare*, Through Isolated Microspore Culture (Protocol without Inhibitors)

*H. vulgare* L. cv. Igri plants were used as donor plants. Seeds were vernalized in soil for one month at 4° C., and then transferred for one month in a plant growth chamber at 18° C. for germination and growth. Finally, plants were transferred to a greenhouse under 18° C. temperature.

Figure 2:
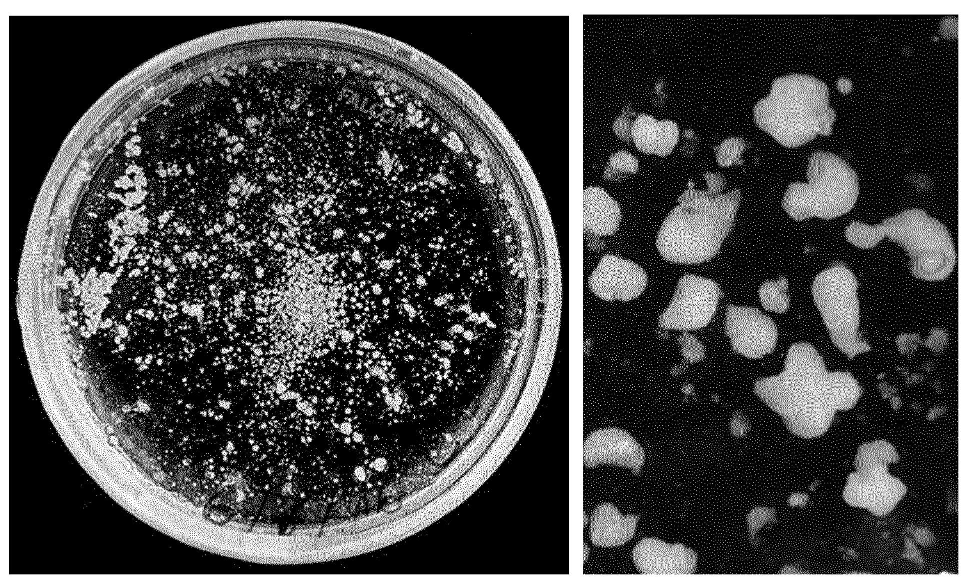
FIG. 2. In vitro microspore embryogenesis in *H. vulgare*. Cotyleoptilar and leaf-stage embryos developed from isolated microspore culture in liquid medium without mammal's kinase inhibitors.

Spikes containing microspores at the stage of vacuolated microspore, the most responsive stage for embryogenesis induction, were collected and surface sterilized by immersion in 5% bleach for 20 min, followed by 4 washes with sterile distilled water. Isolated microspore culture was settled as previously described (Rodríguez-Serrano et al., 2012, Journal of Experimental Botany 63 (5), 2007-2024). The sterilized spikes were pre-treated at 4° C. for 21-24 days as stress treatment to induce microspore embryogenesis. Microspore were isolated blending spikes in 20 ml of pre-cooled 0.4 M mannitol at 4° C., using a Waring Blender pre-cooled in a refrigerator at −20° C., and the extract was filtered through a 100 μm nylon mesh into a beaker pre-cooled at −20° C. The collected microspore suspension was transferred into a 50 ml tube and centrifuged at 800 rpm for 10 min at 4° C. After removing the supernatant, the pellet was resuspended in 4 ml of pre-cooled 0.55 μM maltose and transferred in 15 ml falcon tube. 1.5 ml of 0.4 μM mannitol solution were cautiously added unmixed. After gradient centrifugation at 800 rpm for 10 min at 4° C., the interphase band consisting of an almost pure population of vacuolated microspores was resuspended in 0.4M mannitol solution giving a final volume of 10 ml. After counting cells in the Neubauer chamber, the pelleted microspores were diluted in an appropriate volume of KBP medium to obtain a cell density of $1.1\times10^5$ cells per ml, and plated in 30 mm Petri dishes, at a volume of 1 ml per plate. Then, microspore cultures were incubated at 25° C. in the dark, and reprogrammed microspores and produced multicellular structures/proembryos that can be found after 4-6 days in culture, as the first sign of embryogenesis initiation. Proembryos further developed and produced coleoptylar and mature embryos (FIG. 2), which were observed after 30 days.

1.3. Microspore Embryogenesis of *Q. suber*, Through Anther Culture (Protocol without Inhibitors)

Branches with several catkins were cut and collected from *Q. suber* trees in the countryside (El Pardo region, Madrid, Spain), during the flowering period (from early May to early-mid June). Cut tips of branches were immediately covered with moist cotton and aluminium foil, and transferred to the laboratory, where they were kept in the dark at 4° C. for several days, until use for in vitro culture. Selected catkins were separated from branches and sterilized by immersion in 70% ethanol for 30-60 s, under vacuum, to aid penetration of the solvent. They were then immersed in 2% sodium hypochlorite with 1% Tween-20 for 20 min, with magnetic stirring. After three washes in sterile distilled water, catkins were prepared for dissection and anther excision.

Anther culture and microspore embryogenesis induction were performed as previously described (Testillano et al. 2018, Forestry Sciences Vol. 84. Springer International Publishing AG. pp. 93-105). Anthers containing vacuolated microspores, the most responsive stage for embryogenesis induction, were carefully excised from sterilized catkins under aseptic conditions and plated in Petri dishes of 90 mm diameter on solid induction medium which contained Sommer medium macronutrients, Murashige and Skoog (MS) micronutrients and vitamins, as well as 30 g/L sacarose and activated charcoal. Anthers were placed in linear arrays of 10-12 anthers each, with a gap of around 5 mm between each anther, and up to 100 anthers per Petri dish. Embryogenesis was induced by stress treatment at 33° C. in darkness for 5 days. After this inductive treatment, the anther cultures were transferred to 25° C. in darkness. In the following 20-30 days, responsive anthers become swollen and proembryos and small proembryogenic masses were visible as very small white structures emerging from the anther interior, breaking the tissues of the anther wall. After some more days, proembryos and proembryogenic masses grew and formed globular embryos by direct and indirect embryogenesis from individual microspores.

Microspore-derived embryogenic masses and embryos were transferred to new plates with proliferation medium which has a similar composition to induction medium except that it does not contain activated charcoal and is supplemented with 0.5 g/L glutamine. They were kept at 25° C. in darkness and sub-cultured every month in the same medium, where embryogenic masses can proliferate and spontaneously originate new globular embryos, which further developed heart-shaped, torpedo and cotyledonary embryos. In proliferation medium, some of these embryos produced new embryos by secondary and recurrent embryogenesis.

1.4. Somatic Embryogenesis of *Q. suber*, Through Immature Zygotic Embryos Culture (Protocol without Inhibitors)

Immature pollinated acorns were collected from *Q. suber* L. (cork oak) trees in the countryside (El Pardo region, Madrid, Spain) during fruit development period (late August and September), transferred to the laboratory and kept at 4° C. for one week before in vitro culture initiation. Immature acorns were selected at the most responsive stage to somatic embryogenesis induction; they are those with small size, around 1 cm diameter, and green colour; they contain immature zygotic embryos at the early cotyledonary stage.

Immature zygotic embryos were carefully excised from the acorns by dissecting the surrounding tissues with the help of scalpel and forceps. After dissection, explants (immature zygotic embryos) were sterilized by immersion in 70% ethanol for 30 s and in 2% sodium hypochlorite for 20 min, followed by three rinses in sterile distilled water of 10 min each. Five explants were placed per plate.

Figure 3:
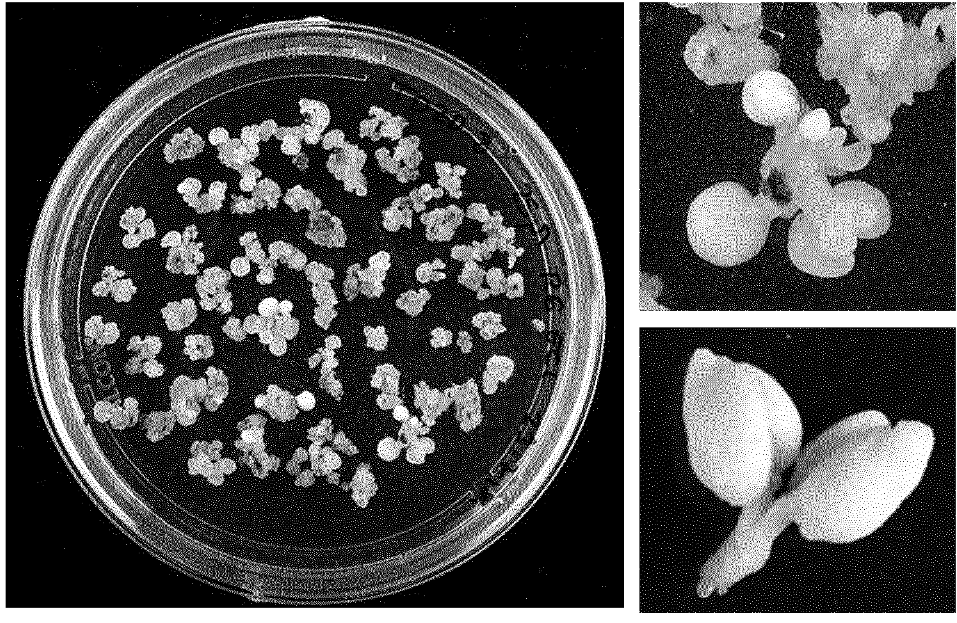
FIG. 3. In vitro somatic embryogenesis in *Q. suber*. Embryos at different developmental stages, cultured in solid medium without mammal's kinase inhibitors, emerging from proembryogenic masses and other embryos, some of them have differentiated fully mature cotyledonary embryos.

Somatic embryogenesis was induced as previously described (Testillano et al. 2018, Plant Cell Culture Protocols, eds. V. M. Loyola-Vargas & N. Ochoa-Alejo. Springer and Bussines Media. pp. 247-256). Explants were first cultured in solid induction medium, which contains Sommer macronutrients, MS micronutrients and vitamins, 0.5 mg/l Glutamine, 30 g/l Sucrose, and 0.5 mg/l 2,4-Dichlorophenoxyacetic acid (2,4-D), for one month at 25° C. and 16/8 h light/darkness. During this induction period, cell reprogramming occurs in some responsive cells which initiated the embryogenesis pathway, producing small proembryogenic masses. Then, the explants were transferred to solid proliferation medium, with the same composition but growth regulator-free (without 2,4-D). During the next weeks of culture in the proliferation medium, proembryogenic masses proliferated and protruded from different parts of the explants; they produce new embryogenic masses and embryos, which in turn give rise to new embryos, that developed to fully developed cotyledonary embryos, by recurrent and secondary embryogenesis (FIG. 3).

1.5. Treatment with Mammal Kinases Inhibitors on Microspore Embryogenesis Cultures of *B. napus* and *H. vulgare* in Liquid Media The compounds were added to the microspore liquid culture media by using stock solutions of 10 mM in DMSO. Appropriate volumes of stock solutions of the drugs were added to the culture media to get the selected working concentrations of the inhibitors, keeping DMSO concentration below 0.2%.

In *B. napus* microspore cultures: 4-benzyl-2-methyl-1,2,4-thiadozilidine-3,5-dione (TDZD8), 5-(2-Morpholin-ethylimino)-2,3-diphenyl-2,5-dihydro-1,2,4-thiadiazole (VP3.15), 3-acetyl-4-(1-methyl-1H-indol-3-yl)-1H- pirrol-2,5-dione (VP3.36), 4-hydroxy-1-ethyl-N'-palmitoyl-2-oxo-1,2-dihydroquinoline-3-carbohydrazide (VP0.7), N-(6-methylbenzothiazole-2-yl)-4-morpholinobenzamide (JZ1.3), N-(6-fluorobenzothiazole-2-yl)-4-morpholinobenzamide, (JZ1.6) and N-(6-bromobenzothiazole-2-yl)-4-morpholinobenzamide (JZ1.24), and (E,Z)-3-(morpholinoimino) indolin-2-one (IGS4.75) were tested at 3-4 different concentrations, ranging from 0.5 to 5 μM.

In *H. vulgare* microspore cultures: 4-benzyl-2-methyl-1,2,4-thiadozilidine-3,5-dione (TDZD8) and N-(6-bromobenzothiazole-2-yl)-4-morpholinobenzamide (JZ1.24) inhibitors at the selected concentrations (2.5 μM and 5μ, respectively) were tested.

The compounds were added from culture initiation and their effect on embryogenesis efficiency was assessed. Several plates of the same cultures were kept without the inhibitors, as controls.

1.6. Evaluation of the Effect of Mammal Kinases Inhibitors Over In Vitro Embryogenesis Induction in Isolated Microspore Cultures of *B. napus* and *H. vulgare*

Embryogenesis induction was quantified in control and treated-cultures by the number of proembryos formed (considered the first sign of embryogenesis initiation), as previously described, and by the number of embryos produced after 40 days. Proembryos were easily identified under inverted microscope in 4 day-culture plates as rounded multicellular structures with higher size and density than microspores, still surrounded by the exine (special microspore wall). Embryos produced after 40 days in culture were quantified through images captured under a stereo microscope.

Randomly obtained micrographs from inverted and stereo microscopes were collected from untreated and treated microspore culture plates. Mean percentage of proembryos and mean number of embryos per plate were obtained from three independent experiments per each in vitro system and treatment. A minimum of 1000 proembryos were counted for each treatment and plant species. Results on proembryos were expressed as percentages (percent change) and referred to the mean percentage of proembryos in control cultures, which has been normalized to 100%.

In order to evaluate whether proembryo structures of treated cultures, identified under the inverted microscope for quantification, were actually dividing microspores, similar to the same structures in control cultures, a simply staining technique was performed to visualize nuclei inside proembryos. Samples from control and treated-cultures of 4 days, containing proembryos, were stained with 10 μg/mL 4',6-diamidine-2-phenyl indole dihydrochloride (DAPI). Squash preparations were analysed under fluorescence microscopy using UV excitation for observing nuclei.

1.7. Evaluation of Quality/Germination Capacity of Embryos Produced after Treatment with Mammal Kinases Inhibitors To evaluate the quality of embryos produced in microspore embryogenesis cultures in the presence of the mammal kinases inhibitors, embryo germination assays were performed. *B. napus* microspore cotyledonary embryos originated from control and treated-cultures were used for in vitro embryo germination and conversion to plantlets as previously described (Prem et al., 2012, BMC Plant Biology 12, 127). The 34-40 old dicotyledonous embryos, after air desiccation on sterile filter paper were germinated in MS medium containing sucrose 2% (w/v) and gelled with 7 g/L bacteriological agar (w/v). Microspore derived-embryos were incubated for 15-20 days at 18° C. in darkness conditions till activation of radicle and plumule, and quantified in terms of percentage of embryos showing normal growth, similar to zygotic embryo germination.

1.8. Treatments with Kinases Inhibitors on Microspore and Somatic Embryogenesis Cultures of *Q. suber* in Solid Media Since the in vitro systems of *Q. suber* were two-step processes in solid culture media, a different strategy than in liquid microspore cultures was applied for the treatments with the mammal kinases inhibitors. During in vitro embryogenesis of *Q. suber*, after incubation in induction medium, the transfer of explants to proliferating medium involves the multiplication of proembryogenic masses, embryogenesis initiation, by recurrent and secondary embryogenesis, and embryo development. Therefore, treatments with the mammal kinases inhibitors were performed during the first 15-30 days in proliferating media, and afterwards, explants with emerging embryos were transferred to fresh proliferating media without the inhibitor.

Since solid media involve much less diffusion and availability of compounds to cells in comparison with liquid media, as referred in other in vitro systems, the concentration of the mammal kinases inhibitors used in solid media was around 10× higher than in liquid media, in the range of 25 to 100 μM. Appropriate volumes of stock solutions of 10 mM in DMSO of the selected compounds were added to cooled media, before its gelling, keeping DMSO concentration below 0.2%. Mock parallel plates of the same cultures were kept as controls.

1.9. Evaluation of the Effect of Inhibitors Over In Vitro Embryogenesis Induction in Microspore and Somatic Embryogenesis Cultures of *Q. suber*

Embryogenesis induction efficiency was quantified in control and treated-cultures by the number of cotyledonary embryos produced by 15-30 days of treatment (culture medium containing the inhibitor) followed by 30 days of recovery (culture medium without inhibitor). Embryo production was estimated as the number of cotyledonary embryos originated per gram of embryogenic masses at culture initiation.

Results 1.1. Effect of Kinases Inhibitors Over Microscope Embryogenesis Cultures *B. napus*

Figure 4:
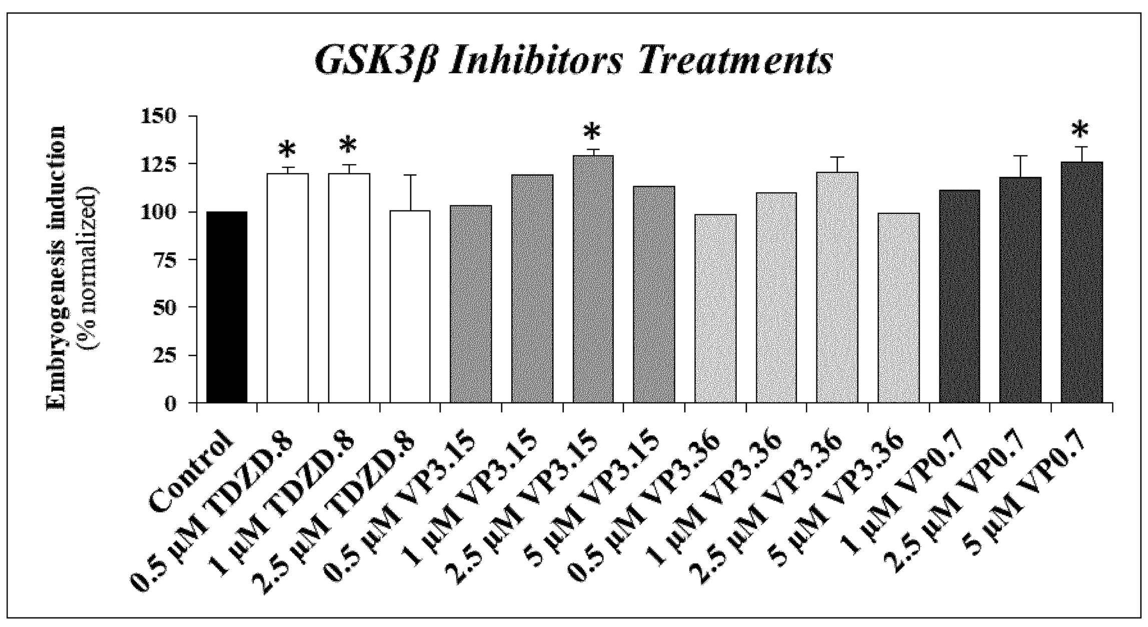
FIG. 4. Effects of four different GSK3β inhibitors (TDZD.8, VP3.15, VP3.36 and VP0.7) over embryogenesis induction efficiency in *B. napus* microspore cultures. Columns indicate percent change of proembryos at 4 days and referred to the mean percentage of proembryos in control cultures which has been normalized to 100%. Asterisks on columns indicate statistically significant differences with control cultures, as assessed by Student's t-test at $P \leq 0.05$.
Figure 5:
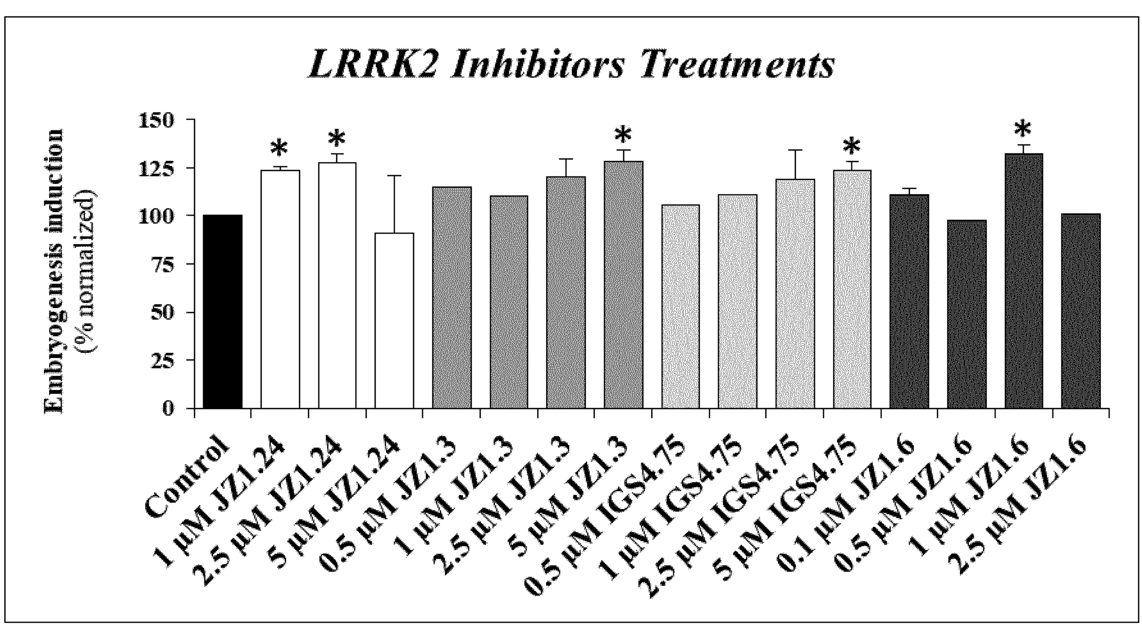
FIG. 5. Effects of four different LRRK2 inhibitors (JZ1.3, JZ1.6, JZ1.24 and IGS4.75) over embryogenesis induction efficiency in *B. napus* microspore cultures. Columns indicate percent change of proembryos at 4 days and refer to the mean percentage of proembryos in control cultures, which has been normalized to 100%. Asterisks on columns indicate statistically significant differences with control cultures, as assessed by Student's t-test at $P \leq 0.05$.

To evaluate the effect of the kinase inhibitors over in vitro embryogenesis induction, we first tested them in *B. napus* microspore embryogenesis, as a model platform to check the mammal kinases inhibitors and different concentrations. After these analyses, one selected mammal kinases inhibitor of each category was tested in other two plant species, *H. vulgare* and *Q. suber*, with different in vitro systems. The efficiency of embryogenesis induction was evaluated in control cultures and cultures treated with the mammal kinases inhibitors, at different concentrations. The results for the GSK3β inhibitors and LRRK2 inhibitors tested are shown as the percentage of proembryos (first sign of embryogenesis initiation) in FIGS. 4 and 5, respectively. The presence of the inhibitors in the culture media affected the production of proembryos in comparison with control cultures, being the proportion of proembryos different depending on the concentration used. Four inhibitors of GSK3β TDZD8; VP3.15, VP3.36, VP0.7 were tested at 3-4 concentrations in the range of 0.1 μM to 5 μM. The results of the quantification of the proembryos produced, as first sign of embryogenesis initiation, in control and treated cultures showed that all inhibitors, at least with one or two of the concentrations used, led to an increase of the production of proembryos (FIGS. 4 and 5). The concentrations and compounds that provided an improvement of embryogenesis initiation yield were the following: GSK3β inhibitors, 0.5 μM and 1 μM TDZD-8, 2.5 μM VP3.15, 2.5 μM VP3.36, and 5 μM VP0.7 (FIG. 4); LRRK2 inhibitors, 2.5 μM JZ1.24, 5 μM JZ1.3, 5 μM IGS4.75, and 1 μM JZ1.6 (FIG. 5). With the other concentrations, treated cultures showed a proportion of proembryos either similar to or slightly higher than control cultures (FIGS. 4 and 5), while they did not show any deleterious/toxic effect.

The results showed that the increase of embryogenesis induction efficiency provided by the use of the inhibitors was in the range of 20-25% for GSK3β inhibitors and 23-30% for LRRK2 inhibitors.

Figure 6:
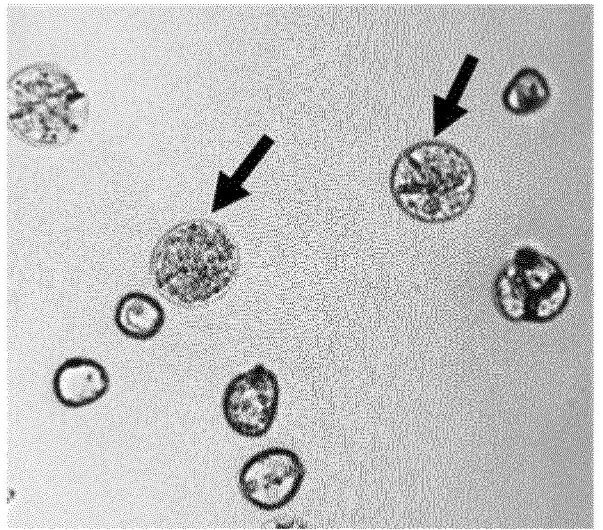
FIG. 6. Proembryos in TDZD.8-treated cultures of microspore embryogenesis of *B. napus*. After 4 days in culture, proembryos (arrows) coexisted with non-responding and dead microspores (smaller structures); DAPI staining (right panel) reveals that proembryos contain several nuclei (arrows), indicating embryogenesis initiation.
Figure 6:
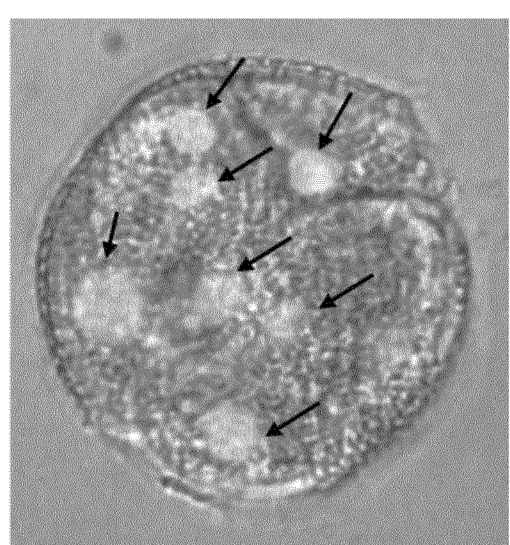

To confirm that proembryos quantified in treated cultures were multicellular microspores that have initiated embryogenesis, squash preparations from control and treated cultures at 4 days were stained with DAPI and observed under fluorescence microscopy. Results showed that proembryos from treated cultures contained several nuclei (FIG. 6), as in control cultures, indicating that they were actually dividing microspores that likely initiated embryogenesis.

Taking into account these results in *B. napus*, the compounds that were selected for testing in other in vitro embryogenesis systems were:

4-benzyl-2-methyl-1,2,4-thiadozilidine-3,5-dione (TDZD.8) as GSK3β inhibitor and N-(6-bromobenzothiazole-2-yl)-4-morpholinobenzamide (JZ1.24) as LRRK2 inhibitor.

Figure 7:
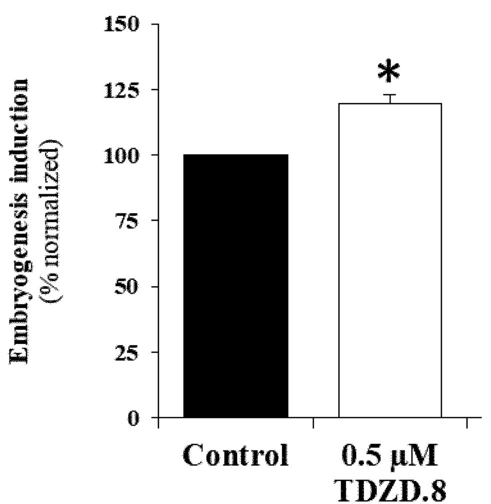
FIG. 7. Effects of TDZD.8 (GSK3β inhibitor) and JZ1.24 (LRRK2 inhibitor) over embryogenesis induction efficiency in *B. napus* microspore cultures. Columns indicate percent change of proembryos at 4 days and refer to the mean percentage of proembryos in control cultures, which has been normalized to 100%. Asterisks on columns indicate statistically significant differences with control cultures, as assessed by Student's t-test at $P \leq 0.05$.
Figure 7:
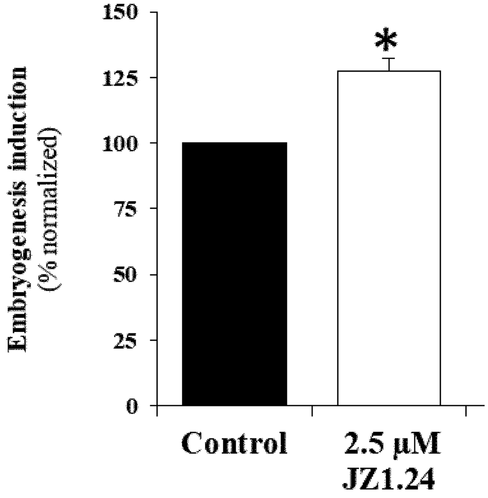

As it is showed in FIG. 7, the selected compounds, the GSK3β inhibitor TDZD.8 and the LRRK2 inhibitor JZ1.24 showed an increase of embryogenesis efficiency, i.e. increase in the percentage of proembryos that was of 20% increase in the case of 0.5 μM TDZD.8, and 27.5% increase in the case of 2.5 μM JZ1.24. in *B. napus* microspore cultures (FIG. 7).

Figure 8:
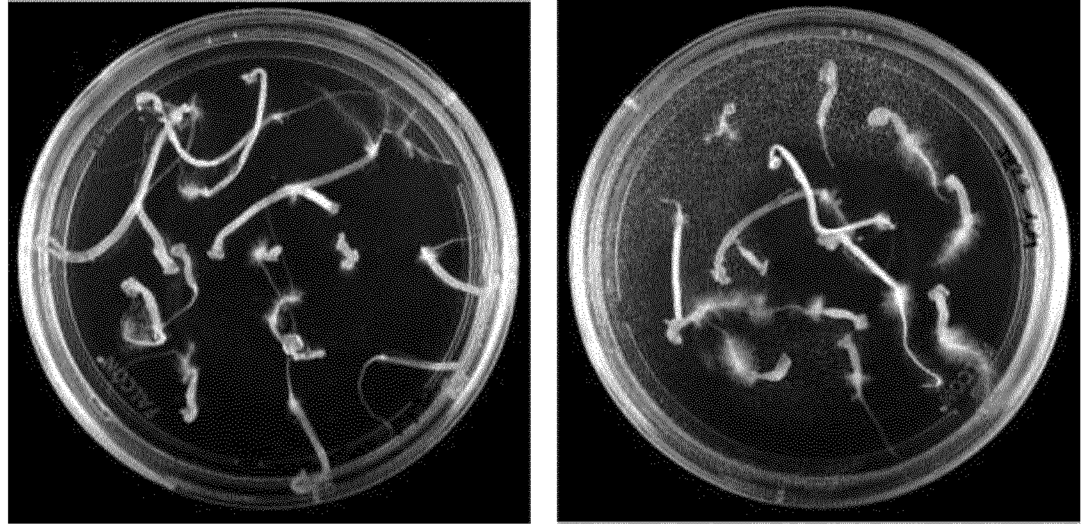
FIG. 8. Evaluation of germination capacity of embryos produced in microspore cultures of *B. napus*. Germinating embryos from control (left) and treated (right) cultures, showing well-developed roots and hypocotyls in most embryos, in both conditions.

The quality of the embryos produced in microspore cultures treated with the mentioned inhibitors was evaluated by germination assays. Fully developed cotyledonary embryos from control and treated cultures, produced after 30 days were desiccated and cultured under germination conditions. Results showed that embryos from treated cultures germinated very well, producing roots and hypocotyl, similarly and in the same proportion than embryos from control cultures (FIG. 8).

1.2. Effect of Kinase Inhibitors Over Microscope Embryogenesis Cultures of *H. vulgare*

Figure 9:
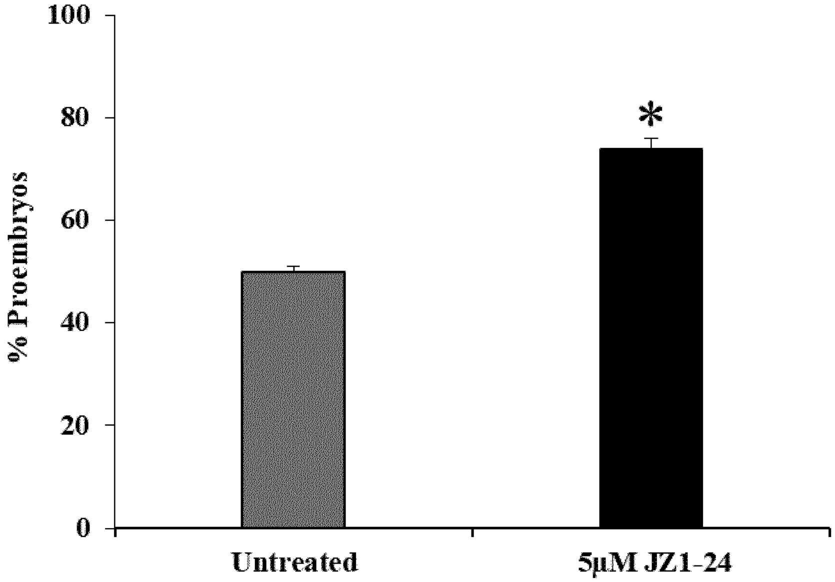
FIG. 9. Effects of selected GSK3β and LRRK2 inhibitors (TDZD.8 and JZ1.24, respectively) over embryogenesis induction efficiency in *H. vulgare* microspore cultures. Columns indicate percent change of proembryos at 4 days in control (untreated) and treated cultures. Asterisks on columns indicate statistically significant differences with control cultures, as assessed by Student's t-test at $P \leq 0.05$.
Figure 9:
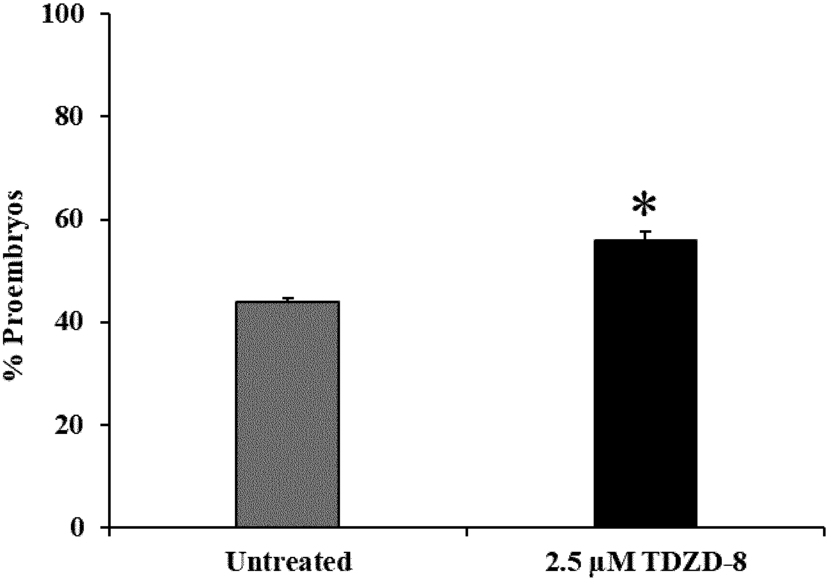

The selected inhibitors, TDZ.8 and JZ1.24 were tested in microspore embryogenesis cultures of a different crop, *H. vulgare*. The inhibitors were firstly applied at the same concentrations that provided the best results in *B. napus,* 0.5 μM TDZD8 and 2.5 μM JZ1.24, but the results obtained (percentage of proembryos) in *H. vulgare* treated cultures using these concentrations were similar to control cultures. Therefore, two slightly higher concentrations were tested for both inhibitors (1 μM and 2.5 μM for TDZD8; and 2.5 μM and 5 μM for JZ1.24). The results showed that the two inhibitors lead to an increase in the embryogenesis initiation in *H. vulgare*, when used at slightly different concentrations than in *B. napus,* 2.5 μM TDZD8 and 5 μM JZ1.24. This indicates that optimal concentrations of these inhibitors could differ among species, probably due to differences in cell wall and permeability properties, and the specific features of each plant and in vitro system. The quantification of the proembryos formed at 4 days showed that treatments with the two inhibitors at the selected concentrations enhanced embryogenesis induction efficiency in *H. vulgare*, being the increase in proembryo formation of 27% in the case of 2.5 μM TDZD8, and 47% in the case of 5 μM JZ1.24-treated cultures (FIG. 9).

Figure 10:
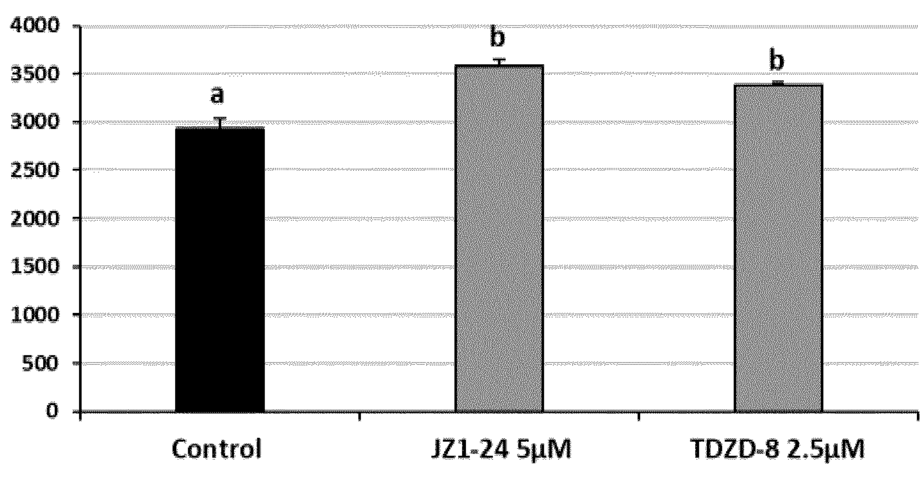
FIG. 10. Effects of selected GSK3β and LRRK2 inhibitors (TDZD.8 and JZ1.24) over embryo production in *H. vulgare* microspore cultures. Columns indicate mean number of embryos per plate formed at 40 days in control (untreated) and treated cultures. Different letters on columns indicate significant differences according to ANOVA and Tukey's tests at $P \leq 0.05$.

Untreated and treated cultures further developed and total number of embryos produced per plate at 40 days was quantified. Microspore cultures treated with these inhibitors produced more embryos than control cultures, being the increment of 22% for JZ1.24 and 15% for TDZD8 (FIG. 10).

The results indicated that small molecule inhibitors of mammalian GSK3β and LRRK2 produced a similar promoting effect in *H. vulgare* than in *B. napus* microspore cultures, an increase of in vitro embryogenesis induction efficiency.

1.3. Effect of Kinase Inhibitors Over Microspore and Somatic Embryogenesis Cultures of *Q. suber*

In order to evaluate the possibility to extend the findings from *B. napus* and *H. vulgare* to more distant species and processes, the selected inhibitors, TDZD.8 and JZ1.24, were applied to a forest woody species *Q. suber*, in which two different embryogenesis in vitro systems were established, somatic embryogenesis from immature zygotic embryos and microspore embryogenesis, two culture systems that consisted in two-step cultures in solid media.

Figure 11:
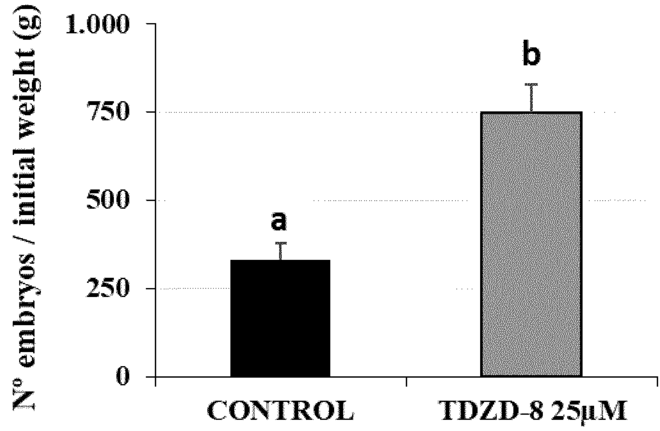
FIG. 11: Effects of selected GSK3β and LRRK2 inhibitors (TDZD.8 and JZ1.24) over embryo production in *Q. suber* somatic embryogenesis. Columns indicate mean number of embryos per gram of initial explant, in control (untreated) and treated cultures. Different letters on columns indicate significant differences according to ANOVA and Tukey's tests at $P \leq 0.05$.
Figure 11:
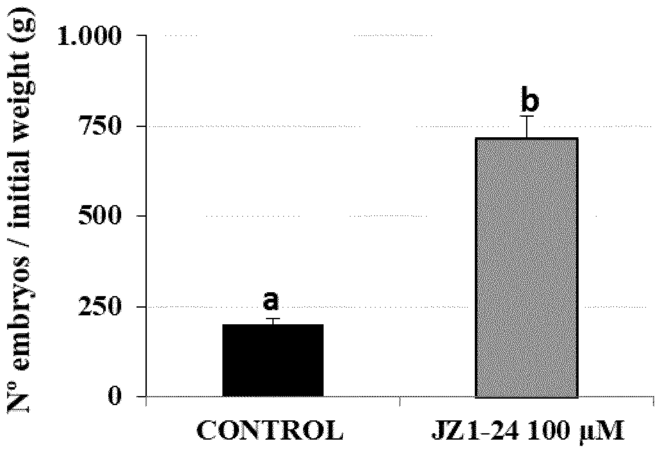
Figure 12:
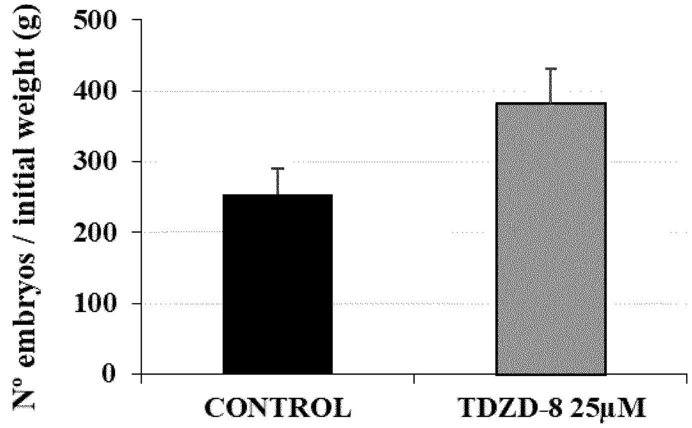
FIG. 12: Effects of selected GSK3β and LRRK2 inhibitors (TDZD.8 and JZ1.24) over embryo production in *Q. suber* microspore embryogenesis. Columns indicate mean number of embryos per gram of initial explant, in control (untreated) and treated cultures. Asterisks on columns indicate statistically significant differences with control cultures, as assessed by Student's t-test at $P \leq 0.05$.
Figure 12:
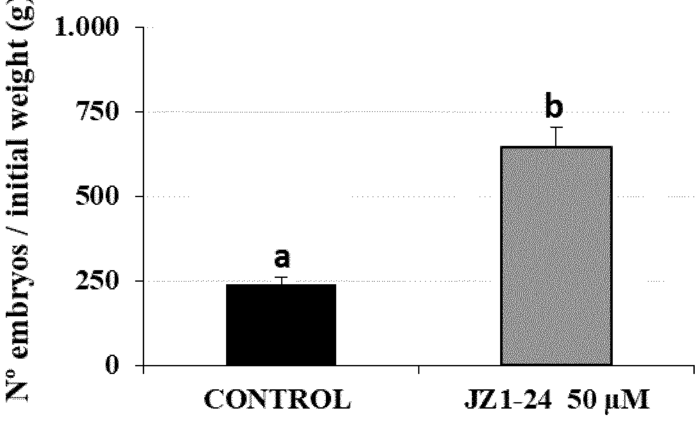

Inhibitor treatments were applied at concentrations 10× higher than in liquid media, because of the lower diffusion and availability of compounds in gelled medium. The evaluation of the effects of the compounds over embryogenesis efficiency in the two systems were assessed by the quantification of the embryos produced in control and treated cultures. Results showed that treatments with the two types of inhibitors increased embryogenesis induction efficiency and lead to higher embryo production, in somatic embryogenesis from immature zygotic embryos cultures (FIG. 11), as well as in microspore embryogenesis from anther cultures (FIG. 12).

The results indicated that also in a woody species and in different in vitro embryogenesis systems, involving solid culture media, the small molecule inhibitors of mammalian GSK3β and LRRK2 produced the same effect than in rapeseed and barley systems in liquid media, an increase of in vitro embryogenesis induction efficiency.

CONCLUSIONS

The present invention deals with a major challenge of in vitro plant propagation techniques, that is to improve the efficiency of embryogenesis induction for rapid production of high numbers of high quality, disease-free and uniform planting material for agroindustry companies, reducing time and costs, in many species of economic interest. The new strategy reported in the present invention uses for the first time in plant in vitro systems inhibitors of mammalian protein kinases, specifically inhibitors of GSK3β and LRRK2 families, which have demonstrated capacity to increase embryogenesis induction and embryo production yield in three different crop and forest species. Moreover, treatments with these inhibitors have been successfully applied to different in vitro protocols, in liquid or solid media, and with direct, indirect and secondary/recurrent embryogenesis, providing similar promoting effects over embryogenesis. Several inhibitors of each group, with different molecular structure, have shown to be able to enhance embryogenesis efficiency, giving additional support to the use of these type of small molecules as new tools to optimize in vitro plant embryogenesis protocols.

2. Synthesis and Characterisation of the Inhibitors of the Present Invention.

2.1. Inhibitors of Formula (I)

4-benzyl-2-methyl-1,2,4-thiadozilidine-3,5-dione (TDZD8) is disclosed in Martinez A et al. (Martinez A et al. J Med Chem. 2002; 45 (6): 1292-9).

2.2. Inhibitors of Formula (II)

All of inhibitors of Formula (II), including 5-(2-Morpholinethylimino)-2,3-diphenyl-2,5-dihydro-1,2,4-thiadiazole (VP3.15), are disclosed in EP2484670A1.

2.3. Inhibitors of Formula (III)

3-acetyl-4-(1-methyl-1H-indol-3-yl)-1H-pirrol-2,5-dione (VP3.36) is disclosed in Perez D I et al. (Perez D I et al. J Med Chem. 2011; 54 (12): 4042-56).

2.4. Inhibitors of Formula (IV)

4-hydroxy-1-ethyl-N'-palmitoyl-2-oxo-1,2-dihydroquinoline-3-carbohydrazide (VP0.7) is disclosed in Palomo V et al. (Palomo V et al. J Med Chem. 201; 60 (12): 4983-5001).

2.5. Inhibitors of Formula (V)

N-(benzothiazole-2-yl)-4-morpholinobenzamide: 276.0 mg of 4-morpholinobenzoic acid (1.3 mmol), 331.00 mg of EDCl (1.4 mmol), 24.4 mg of DMAP (0.3 mmol) and 335 μL (2.4 mmol) of triethylamine were dissolved in dichloromethane. After stirring for 1 hour at room temperature, 200 mg of 2-aminobenzothiazole (1.3 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by chromatography in a flash column using a mixture of eluents $CH_2Cl_2$/MeOH (20:1) to obtain a yellow solid (72 mg, 16%). HPLC Purity >95%. MS: m/z 340 $[M+1]^+$. $^1H$ NMR (300 MHz, $CDCl_3$) δ 10.21 (s, 1H, NH), 7.90 (d, J=9.0 Hz, 2H), 7.84 (dd, J=8.5, 1.5 Hz, 1H), 7.62 (dd, J=8.3, 1.2 Hz, 1H), 7.44-7.35 (m, 1H), 7.35-7.27 (m, 1H), 4.01-3.71 (m, 4H), 3.49-3.16 (m, 4H). $^{13}C$ NMR (75 MHz, DMSO-$d_6$) δ 164.6, 159.1, 154.3, 148.2, 132.2, 129.4, 126.0, 123.7, 121.3, 121.1, 120.7, 113.8, 66.5, 47.4.

N-(6-methoxybenzothiazole-2-yl)-4-morpholinobenzamide: 230.0 mg of 4-morpholinobenzoic acid (1.1 mmol), 276.6 mg of EDCl (1.4 mmol), 24.43 mg of DMAP (0.2 mmol) and 248 μL (1.7 mmol) of triethylamine were dissolved in dichloromethane. After stirring for 1 hour at room temperature, 200 mg of 2-amino-6-methoxybenzothiazole (1.1 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by flash column chromatography using a mixture of eluents $CH_2Cl_2$/MeOH (50:1) to obtain a yellow solid (36 mg, 9%). P.f.: 237.6-240.0° C. HPLC Purity: 95%. MS: m/z 370 $[M+H]^+$. $^1H$ NMR (300 MHz, $CDCl_3$) δ 9.47 (s, 1H), 7.88 (d, J=9.0 Hz, 2H), 7.64 (d, J=8.8 Hz, 1H), 7.33 (d, J=2.6 Hz, 1H), 7.04 (dd, J=8.8, 2.6 Hz, 1H), 6.94 (d, J=9.0 Hz, 2H), 3.93-3.83 (m, 7H), 3.36-3.31 (m, 4H). $^{13}C$ NMR (75 MHz, DMSO-$d_6$) δ 164.8, 156.9, 156.0, 153.8, 142.7, 132.8, 129.8, 120.8, 120.5, 114.80, 113.1, 104.6, 65.8, 55.6, 46.8.

N-(6-trifluoromethylbenzothiazole-2-yl)-4-morpholinobenzamide: 189.9 mg of 4-morpholinobenzoic acid (0.9 mmol), 228.53 mg of EDCl (1.2 mmol), 22.41 mg of DMAP (0.2 mmol) and 223 L (1.5 mmol) of triethylamine were dissolved in dichloromethane. After stirring for 1 hour at room temperature, 200 mg of 2-amino-6-trifluorobenzothiazole (0.9 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by automatic flash column chromatography (Biotage@Isolera One) using a mixture of eluents hexane/AcOEt to obtain a yellow solid (79 mg, 26%). P.f.: 218.5-218.5° C. HPLC Purity: 95%. MS: m/z 408 $[M+H]^+$. $^1H$ NMR (300 MHz, $CDCl_3$) δ 10.85 (s, 1H), 8.13 (s, 1H), 7.89 (d, J=9.0 Hz, 1H), 7.57-7.53 (m, 2H), 6.84 (d, J=9.0 Hz, 2H), 3.87-3.83 (m, 4H), 3.31-3.26 (m, 4H). $^{13}C$ NMR (75 MHz, $CDCl_3$) δ 163.8, 160.8, 153.4, 149.4, 131.2, 128.5, 124.9 (d, J=32.5 Hz), 124.3, 122.1 (d, J=3.4 Hz), 119.6 (d, J=32.2 Hz), 118.0 (d, J=4.2 Hz), 112.7, 65.4, 46.3, 28.6. $C_{19}H_{16}F_3N_3O_2S$: Theoretical (%) C, 56.01; H, 3.96; N, 10.31; S, 7.87. Found (%) C, 56.13; H, 3.98; N, 10.38; S, 7.59.

N-(6-methylbenzothiazole-2-yl)-4-morpholinobenzamide (JZ1.3): 252.4 mg of 4-morpholinobenzoic acid (1.2 mmol), 303.5 mg of EDCl (1.58 mmol), 20.06 mg of DMAP (0.2 mmol) and 272 μL (1.9 mmol) of triethylamine were dissolved in dichloromethane. After stirring for 1 hour at room temperature, 200 mg of 2-amino-6-methylbenzothiazole (1.2 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage@Isolera One) using a mixture of eluents hexane/AcOEt to obtain a yellow solid (43 mg, 10%). P.f.: 287.7-288.8° C. MS (ESI+): m/z 354 $[M+H]^+$. $^1H$ NMR (300 MHz, $CDCl_3$) δ 10.56 (s, 1H), 7.89 (d, J=8.9 Hz, 2H), 7.63 (s, 1H), 7.42 (d, J=8.3 Hz, 1H), 7.16 (dd, J=8.3, 1.7 Hz, 1H), 6.85 (d, J=8.9 Hz, 1H), 3.87-3.83 (m, 4H), 3.29-3.26 (m, 4H), 2.46 (s, 3H). $^{13}C$ NMR (75 MHz, $CDCl_3$) δ 164.7, 158.5, 154.2, 146.1, 133.7, 132.3, 129.4, 127.5, 121.3, 121.1, 120.3, 113.8, 66.5, 47.5, 21.4. $C_{19}H_{19}N_3O_2S$: Theoretical (%) C, 64.57; H, 5.42; N, 11.89; S, 9.07. Found (%) C, 64.33; H, 5.38; N, 11.85; S, 8.96.

N-(6-chlorobenzothiazole-2-yl)-4-morpholinobenzamide: 224.4 mg of 4-morpholinobenzoic acid (1.1 mmol), 269.89 mg of EDCl (1.4 mmol), 26.4 mg of DMAP (0.2 mmol) and 242 μL (1.7 mmol) of triethylamine were dissolved in dichloromethane. After stirring for 1 hour at room temperature, 200 mg of 2-amino-6-chlorobenzothiazole (1.1 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage@Isolera One) using a mixture of eluents hexane/AcOEt to obtain a white solid (96 mg, 24%). P.f.: 245.4-246.4° C. HPLC Purity: 97%. MS: m/z 374 $[M+H]^+$. $^1H$ NMR (300 MHz, $CDCl_3$) δ 10.25 (s, 1H), 7.89 (d, J=8.9 Hz, 2H), 7.81 (d, J=2.1 Hz, 1H), 7.52 (d, J=8.7 Hz, 1H), 7.33 (dd, J=8.7, 2.1 Hz, 1H), 6.89 (d, J=9.0 Hz, 2H), 3.92-3.82 (m, 4H), 3.33-3.30 (m, 4H). $^{13}C$ NMR (75 MHz, $CDCl_3$) δ 164.5, 159.3, 154.4, 146.8, 139.7, 133.5, 129.4, 126.7, 121.5, 121.0, 120.8, 113.7, 66.5, 47.4. $C_{18}H_{16}ClN_3O_2S$: Theoretical (%) C, 57.83; H, 4.31; N, 11.24; S, 8.58. Found (%) C, 57.56; H, 4.09; N, 11.43; S, 8.40.

N-(6-fluorobenzothiazole-2-yl)-4-morpholinobenzamide (JZ1.6): 168.20 mg of 4-morpholinobenzoic acid (1.2 mmol), 296.3 mg of EDCl (1.5 mmol), 29.05 mg of DMAP (0.2 mmol) and 265 L (1.9 mmol) of triethylamine were dissolved in dichloromethane. After stirring for 1 hour at room temperature, 200 mg of 2-amino-6-fluorobenzothiazole (1.2 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage@Isolera One) using a mixture of eluents hexane/AcOEt to obtain a white solid (79 mg, 19%). P.f.: 228.3-229.3° C. HPLC Purity: 98%. MS: m/z 358 $[M+H]^+$. $^1H$ NMR (300 MHz, $CDCl_3$) δ 9.96 (s, 1H), 7.81 (d, J=8.9 Hz, 2H), 7.74 (d, J=2.1 Hz, 1H), 7.49 (d, J=8.6 Hz, 1H), 7.28 (dd, J=8.7, 2.1 Hz, 1H), 6.84 (d, J=8.7 Hz, 2H), 3.87-3.85 (m, 4H), 3.34-3.30 (m, 4H). $^{13}C$ NMR (75 MHz, $CDCl_3$) δ 164.4, 159.2, 154.4, 147.0, 138.7, 133.6, 129.3, 126.8, 121.6, 121.0, 120.8, 113.8, 66.5, 47.4. $C_{18}H_{16}FN_3O_2S$: Theoretical (%) C, 60.49; H, 4.51; N, 11.76; S, 8.97. Found (%) C, 60.68; H, 4.50; N, 11.55; S, 8.72.

N-(6-ethoxybenzothiazole-2-yl)-4-morpholinobenzamide: 213.1 mg of 4-morpholinobenzoic acid (1.0 mmol), 256.2 mg of EDCl (1.3 mmol), 25.12 mg of DMAP (0.2 mmol) were dissolved in dichloromethane. After stirring for 6 hours at room temperature, 200 mg of 2-amino-6-ethoxybenzothiazole (1.0 mmol) and 229 μL of triethylamine (1.9 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage@Isolera One) using a mixture of eluents hexane/AcOEt to obtain a yellow solid (20 mg, 5%). P.f.: 222.8-223.8° C. HPLC Purity: 95%. MS: m/z 384 $[M+H]^+$. $^1H$ NMR (300 MHz, $CDCl_3$) δ 8.07 (d, J=8.6 Hz, 2H), 7.54 (d, J=8.9 Hz, 1H), 7.35-7.18 (m, 1H), 7.04 (dd, J=8.9, 2.4 Hz, 1H), 6.89 (d, J=8.6 Hz, 2H), 4.07 (q, J=6.9 Hz, 2H), 3.89-3.69 (m, 4H), 3.38-3.25 (m, 4H), 1.43 (t, J=6.9 Hz, 3H). $^{13}C$ NMR (75 MHz, $CDCl_3$) δ 164.4, 157.1, 156.0, 154.2, 142.3, 133.3, 129.3, 121.3, 121.2, 119.7, 115.5, 114.2, 113.8, 106.0, 104.9, 99.5, 66.5, 64.1, 64.1, 47.5, 14.8.

N-(6-bromobenzothiazole-2-yl)-4-morpholinobenzamide (JZ1.24): 180.9 mg of 4-morpholinobenzoic acid (0.9 mmol), 217.6 mg of EDCl (1.1 mmol), 21.33 mg of DMAP (0.2 mmol) were dissolved in dichloromethane. After stirring for 6 hours at room temperature, 200 mg of 2-amino-6-bromobenzothiazole (0.9 mmol) and 195 μl of triethylamine (1.4 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a yellow solid (41 mg, 11%). P.f.: 237.5-238.5° C. HPLC Purity: 98%. MS: m/z 418 [M+H]+. $^1H$ NMR (300 MHz, $CDCl_3$) δ 10.51 (s, 1H), 7.96 (s, 1H), 7.87 (d, J=9.0 Hz, 3H), 7.44 (dd, J=8.6, 1.9 Hz, 2H), 7.38 (d, J=8.6 Hz, 2H), 6.86 (d, J=9.0 Hz, 3H), 3.89-3.83 (m, 11H), 3.33-3.26 (m, 11H). $^{13}C$ NMR (75 MHz, $CDCl_3$) δ 165.2, 160.4, 154.8, 147.1, 134.1, 130.0, 129.9, 124.3, 122.1, 121.1, 117.2, 114.1, 66.9, 47.8.

N-(6-propoxybenzothiazole-2-yl)-4-morpholinobenzamide: 248.8 mg of 4-morpholinobenzoic acid (1.2 mmol), 299.00 mg of EDCl (1.6 mmol), 29.3 mg of DMAP (0.2 mmol) were dissolved in dichloromethane. After stirring for 6 hours at room temperature, 250 mg of 2-amino-6-propoxybenzothiazole (1.2 mmol) and 267.6 μL (1.9 mmol) of triethylamine were added. The reaction is left under stirring at room temperature during the night. After this time period the crude was washed with a HCl solution (0.1M). Next, the organic phase is dried on anhydrous magnesium sulfate, the solvent is evaporated at low pressure and is purified by flash column chromatography using a mixture of eluents $CH_2Cl_2$/MeOH (50:1) to obtain a yellow solid (127 mg, 27%). HPLC Purity>95%. MS: m/z 398 [M+H]+. $^1H$ NMR (300 MHz, $CDCl_3$) δ 7.88 (d, J=9.0 Hz, 2H), 7.46 (d, J=8.9 Hz, 1H), 7.31 (d, J=2.5 Hz, 1H), 6.96 (dd, J=8.9, 2.5 Hz, 1H), 6.88 (d, J=9.0 Hz, 2H), 3.98 (t, J=6.6 Hz, 2H), 3.89-3.83 (m, 4H), 3.32-3.27 (m, 4H), 1.85 (h, J=7.3 Hz, 2H), 1.06 (t, J=7.4 Hz, 2H). $^{13}C$ NMR (75 MHz, $CDCl_3$) δ 163.6, 156.3, 155.2, 153.3, 141.27, 132.2, 128.4, 120.4, 120.3, 114.5, 112.8, 103.9, 69.2, 65.5, 46.5, 21.6, 9.5. $C_{21}H_{23}N_3O_3S$: Theoretical (%) C, 63.46; H, 5.83; N, 10.57; S, 8.07. Found (%) C, 63.73; H, 5.74, N, 10.09; S, 7.71.

N-(6-isopropylbenzothiazole-2-yl)-4-morpholinobenzamide: 269.4 mg of 4-morpholinobenzoic acid (1.3 mmol), 324.00 mg of EDCl (1.7 mmol), 32.00 mg of DMAP (0.3 mmol) were dissolved in dichloromethane. After stirring for 6 hours at room temperature, 250 mg of 2-amino-6-isopropylbenzothiazole (1.3 mmol) and 290.0 μL (2.1 mmol) of triethylamine were added. The reaction is left under stirring at room temperature during the night. After this time period the crude was washed with a HCl solution (0.1M). Next, the organic phase is dried on anhydrous magnesium sulfate, the solvent is evaporated at low pressure and is purified by flash column chromatography using a mixture of eluents $CH_2Cl_2$/MeOH (50:1) to obtain a yellow solid (218.4 mg, 44%). HPLC Purity>95%. MS: m/z 382 $[M+H]^+$. $^1H$ NMR (300 MHz, $CDCl_3$) δ 10.35 (s, 1H), 7.89 (d, J=9.0 Hz, 2H), 7.68 (d, J=1.7 Hz, 1H), 7.49 (d, J=8.4 Hz, 1H), 7.26-7.22 (m, 1H), 6.88 (d, J=9.0 Hz, 2H), 3.89-3.81 (m, 4H), 3.33-3.25 (m, 4H), 3.03 (p, J=6.9 Hz, 1H), 1.31 (d, J=6.9 Hz, 6H). $^{13}C$ NMR (75 MHz, $CDCl_3$) δ 163.7, 157.7, 153.2, 145.3, 143.9, 131.3, 128.4, 124.0, 120.4, 119.4, 119.1, 117.5, 112.8, 65.5, 46.5, 33.2, 23.3. $C_{21}H_{23}N_3O_2S$: Theoretical (%) C, 66.12; H, 6.08; N, 11.00; S, 8.40. Found (%) C, 66.09; H, 6.13; N, 10.69; S, 8.54.

2.6. Inhibitor of formula (E,Z)-3-(morpholinoimino) indolin-2-one (IGS4.75): is disclosed in Salado IG. et al., (Salado IG. et al., *Eur J Med Chem.* 2017 Sep. 29; 138:328-342).

The invention claimed is:

1. A method to induce in vitro plant embryogenesis, said method comprising:

a. culturing microspores and/or explants in a culture medium suitable for embryo development; and b. adding mammal kinase inhibitors to the culture medium of a); and c. culturing for a period sufficient to obtain embryos, wherein the mammal kinases inhibitor is selected from a list consisting of: 4-benzyl-2-methyl-1,2,4-thiadozilidine-3,5-dione (TDZD8), 5-(2-Morpholinethylimino)-2,3-diphenyl-2,5-dihydro-1,2,4-thiadiazole (VP3.15), 3-acetyl-4-(1-methyl-1H-indol-3-yl)-1H-pirrol-2,5-dione (VP3.36), 4-hydroxy-1-ethyl-N'-palmitoyl-2-oxo-1,2-dihydroquinoline-3-carbohydrazide (VP0.7), N-(6-methylbenzothiazole-2-yl)-4-morpholinobenzamide (JZ1.3), N-(6-fluorobenzothiazole-2-yl)-4-morpholinobenzamide, (JZ1.6), N-(6-bromobenzothiazole-2-yl)-4-morpholinobenzamide (JZ1.24) and (E,Z)-3-(morpholinoimino) indolin-2-one (IGS4.75).

2. The method according to claim 1 wherein the mammal kinases are human kinases.

3. The method according to claim 1 wherein the embryogenesis is somatic or by microspores.

4. The method according to claim 1 wherein the plants are crops plants or forest plants.

5. The method according to claim 1 wherein the mammal kinase inhibitor concentration ranges from 0.5 μM to 100 μM.

6. The method according to claim 2, wherein the human kinases are GSK3β or LRRK2.

7. The method according to claim 6, wherein the kinase GSK3β comprises the sequence selected from the list consisting of SEQ ID NO: 1 to 4, and the kinase LRRK2 comprises the sequence selected from the list consisting of SEQ ID NO: 5 to 7.

8. The method according to claim 4, wherein the crops plants are *Brassica* spp, or *Hordeum* spp.

9. The method according to claim 4, wherein the forest plant is *Quercus* spp.

* * * * *

SEQUENCE LISTING

```
<160> NUMBER OF SEQ ID NOS: 7

<210> SEQ ID NO 1
<211> LENGTH: 420
<212> TYPE: PRT
```

-continued

<213> ORGANISM: Homo sapiens

<400> SEQUENCE: 1

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Thr Pro Thr Asn Ala Thr Ala Ala Ser Asp Ala
385                 390                 395                 400
```

-continued

```
Asn Thr Gly Asp Arg Gly Gln Thr Asn Asn Ala Ala Ser Ala Ser Ala
                405                 410                 415

Ser Asn Ser Thr
            420


<210> SEQ ID NO 2
<211> LENGTH: 433
<212> TYPE: PRT
<213> ORGANISM: Homo sapiens

<400> SEQUENCE: 2

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350
```

-continued

```
Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 3
<211> LENGTH: 387
<212> TYPE: PRT
<213> ORGANISM: Homo sapiens

<400> SEQUENCE: 3

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285
```

```
Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Asp Ala Asn
        355                 360                 365

Thr Gly Asp Arg Gly Gln Thr Asn Asn Ala Ala Ser Ala Ser Ala Ser
    370                 375                 380

Asn Ser Thr
385


<210> SEQ ID NO 4
<211> LENGTH: 400
<212> TYPE: PRT
<213> ORGANISM: Homo sapiens

<400> SEQUENCE: 4

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
```

-continued

```
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Asp Ala Asn Thr Gly Asp
    370                 375                 380

Arg Gly Gln Thr Asn Asn Ala Ala Ser Ala Ser Ala Ser Asn Ser Thr
385                 390                 395                 400


<210> SEQ ID NO 5
<211> LENGTH: 2527
<212> TYPE: PRT
<213> ORGANISM: Homo sapiens

<400> SEQUENCE: 5

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu Arg Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240
```

-continued

```
Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
    370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
```

-continued

```
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080
```

-continued

Thr Leu Lys Gln Phe Asn Leu Ser Tyr Asn Gln Leu Ser Phe Val
1085 1090 1095

Pro Glu Asn Leu Thr Asp Val Val Glu Lys Leu Glu Gln Leu Ile
1100 1105 1110

Leu Glu Gly Asn Lys Ile Ser Gly Ile Cys Ser Pro Leu Arg Leu
1115 1120 1125

Lys Glu Leu Lys Ile Leu Asn Leu Ser Lys Asn His Ile Ser Ser
1130 1135 1140

Leu Ser Glu Asn Phe Leu Glu Ala Cys Pro Lys Val Glu Ser Phe
1145 1150 1155

Ser Ala Arg Met Asn Phe Leu Ala Ala Met Pro Phe Leu Pro Pro
1160 1165 1170

Ser Met Thr Ile Leu Lys Leu Ser Gln Asn Lys Phe Ser Cys Ile
1175 1180 1185

Pro Glu Ala Ile Leu Asn Leu Pro His Leu Arg Ser Leu Asp Met
1190 1195 1200

Ser Ser Asn Asp Ile Gln Tyr Leu Pro Gly Pro Ala His Trp Lys
1205 1210 1215

Ser Leu Asn Leu Arg Glu Leu Leu Phe Ser His Asn Gln Ile Ser
1220 1225 1230

Ile Leu Asp Leu Ser Glu Lys Ala Tyr Leu Trp Ser Arg Val Glu
1235 1240 1245

Lys Leu His Leu Ser His Asn Lys Leu Lys Glu Ile Pro Pro Glu
1250 1255 1260

Ile Gly Cys Leu Glu Asn Leu Thr Ser Leu Asp Val Ser Tyr Asn
1265 1270 1275

Leu Glu Leu Arg Ser Phe Pro Asn Glu Met Gly Lys Leu Ser Lys
1280 1285 1290

Ile Trp Asp Leu Pro Leu Asp Glu Leu His Leu Asn Phe Asp Phe
1295 1300 1305

Lys His Ile Gly Cys Lys Ala Lys Asp Ile Ile Arg Phe Leu Gln
1310 1315 1320

Gln Arg Leu Lys Lys Ala Val Pro Tyr Asn Arg Met Lys Leu Met
1325 1330 1335

Ile Val Gly Asn Thr Gly Ser Gly Lys Thr Thr Leu Leu Gln Gln
1340 1345 1350

Leu Met Lys Thr Lys Lys Ser Asp Leu Gly Met Gln Ser Ala Thr
1355 1360 1365

Val Gly Ile Asp Val Lys Asp Trp Pro Ile Gln Ile Arg Asp Lys
1370 1375 1380

Arg Lys Arg Asp Leu Val Leu Asn Val Trp Asp Phe Ala Gly Arg
1385 1390 1395

Glu Glu Phe Tyr Ser Thr His Pro His Phe Met Thr Gln Arg Ala
1400 1405 1410

Leu Tyr Leu Ala Val Tyr Asp Leu Ser Lys Gly Gln Ala Glu Val
1415 1420 1425

Asp Ala Met Lys Pro Trp Leu Phe Asn Ile Lys Ala Arg Ala Ser
1430 1435 1440

Ser Ser Pro Val Ile Leu Val Gly Thr His Leu Asp Val Ser Asp
1445 1450 1455

Glu Lys Gln Arg Lys Ala Cys Met Ser Lys Ile Thr Lys Glu Leu
1460 1465 1470

-continued

```
Leu Asn  Lys Arg Gly Phe Pro  Ala Ile Arg Asp Tyr  His Phe Val
    1475                 1480                 1485

Asn Ala  Thr Glu Glu Ser Asp  Ala Leu Ala Lys Leu  Arg Lys Thr
    1490                 1495                 1500

Ile Ile  Asn Glu Ser Leu Asn  Phe Lys Ile Arg Asp  Gln Leu Val
    1505                 1510                 1515

Val Gly  Gln Leu Ile Pro Asp  Cys Tyr Val Glu Leu  Glu Lys Ile
    1520                 1525                 1530

Ile Leu  Ser Glu Arg Lys Asn  Val Pro Ile Glu Phe  Pro Val Ile
    1535                 1540                 1545

Asp Arg  Lys Arg Leu Leu Gln  Leu Val Arg Glu Asn  Gln Leu Gln
    1550                 1555                 1560

Leu Asp  Glu Asn Glu Leu Pro  His Ala Val His Phe  Leu Asn Glu
    1565                 1570                 1575

Ser Gly  Val Leu Leu His Phe  Gln Asp Pro Ala Leu  Gln Leu Ser
    1580                 1585                 1590

Asp Leu  Tyr Phe Val Glu Pro  Lys Trp Leu Cys Lys  Ile Met Ala
    1595                 1600                 1605

Gln Ile  Leu Thr Val Lys Val  Glu Gly Cys Pro Lys  His Pro Lys
    1610                 1615                 1620

Gly Ile  Ile Ser Arg Arg Asp  Val Glu Lys Phe Leu  Ser Lys Lys
    1625                 1630                 1635

Arg Lys  Phe Pro Lys Asn Tyr  Met Ser Gln Tyr Phe  Lys Leu Leu
    1640                 1645                 1650

Glu Lys  Phe Gln Ile Ala Leu  Pro Ile Gly Glu Glu  Tyr Leu Leu
    1655                 1660                 1665

Val Pro  Ser Ser Leu Ser Asp  His Arg Pro Val Ile  Glu Leu Pro
    1670                 1675                 1680

His Cys  Glu Asn Ser Glu Ile  Ile Ile Arg Leu Tyr  Glu Met Pro
    1685                 1690                 1695

Tyr Phe  Pro Met Gly Phe Trp  Ser Arg Leu Ile Asn  Arg Leu Leu
    1700                 1705                 1710

Glu Ile  Ser Pro Tyr Met Leu  Ser Gly Arg Glu Arg  Ala Leu Arg
    1715                 1720                 1725

Pro Asn  Arg Met Tyr Trp Arg  Gln Gly Ile Tyr Leu  Asn Trp Ser
    1730                 1735                 1740

Pro Glu  Ala Tyr Cys Leu Val  Gly Ser Glu Val Leu  Asp Asn His
    1745                 1750                 1755

Pro Glu  Ser Phe Leu Lys Ile  Thr Val Pro Ser Cys  Arg Lys Gly
    1760                 1765                 1770

Cys Ile  Leu Leu Gly Gln Val  Val Asp His Ile Asp  Ser Leu Met
    1775                 1780                 1785

Glu Glu  Trp Phe Pro Gly Leu  Leu Glu Ile Asp Ile  Cys Gly Glu
    1790                 1795                 1800

Gly Glu  Thr Leu Leu Lys Lys  Trp Ala Leu Tyr Ser  Phe Asn Asp
    1805                 1810                 1815

Gly Glu  Glu His Gln Lys Ile  Leu Leu Asp Asp Leu  Met Lys Lys
    1820                 1825                 1830

Ala Glu  Glu Gly Asp Leu Leu  Val Asn Pro Asp Gln  Pro Arg Leu
    1835                 1840                 1845

Thr Ile  Pro Ile Ser Gln Ile  Ala Pro Asp Leu Ile  Leu Ala Asp
    1850                 1855                 1860

Leu Pro  Arg Asn Ile Met Leu  Asn Asn Asp Glu Leu  Glu Phe Glu
```

-continued

```
    1865                1870                1875

Gln Ala  Pro Glu Phe Leu Leu  Gly Asp Gly Ser Phe  Gly Ser Val
    1880                1885                1890

Tyr Arg  Ala Ala Tyr Glu Gly  Glu Glu Val Ala Val  Lys Ile Phe
    1895                1900                1905

Asn Lys  His Thr Ser Leu Arg  Leu Leu Arg Gln Glu  Leu Val Val
    1910                1915                1920

Leu Cys  His Leu His His Pro  Ser Leu Ile Ser Leu  Leu Ala Ala
    1925                1930                1935

Gly Ile  Arg Pro Arg Met Leu  Val Met Glu Leu Ala  Ser Lys Gly
    1940                1945                1950

Ser Leu  Asp Arg Leu Leu Gln  Gln Asp Lys Ala Ser  Leu Thr Arg
    1955                1960                1965

Thr Leu  Gln His Arg Ile Ala  Leu His Val Ala Asp  Gly Leu Arg
    1970                1975                1980

Tyr Leu  His Ser Ala Met Ile  Ile Tyr Arg Asp Leu  Lys Pro His
    1985                1990                1995

Asn Val  Leu Leu Phe Thr Leu  Tyr Pro Asn Ala Ala  Ile Ile Ala
    2000                2005                2010

Lys Ile  Ala Asp Tyr Gly Ile  Ala Gln Tyr Cys Cys  Arg Met Gly
    2015                2020                2025

Ile Lys  Thr Ser Glu Gly Thr  Pro Gly Phe Arg Ala  Pro Glu Val
    2030                2035                2040

Ala Arg  Gly Asn Val Ile Tyr  Asn Gln Gln Ala Asp  Val Tyr Ser
    2045                2050                2055

Phe Gly  Leu Leu Leu Tyr Asp  Ile Leu Thr Thr Gly  Gly Arg Ile
    2060                2065                2070

Val Glu  Gly Leu Lys Phe Pro  Asn Glu Phe Asp Glu  Leu Glu Ile
    2075                2080                2085

Gln Gly  Lys Leu Pro Asp Pro  Val Lys Glu Tyr Gly  Cys Ala Pro
    2090                2095                2100

Trp Pro  Met Val Glu Lys Leu  Ile Lys Gln Cys Leu  Lys Glu Asn
    2105                2110                2115

Pro Gln  Glu Arg Pro Thr Ser  Ala Gln Val Phe Asp  Ile Leu Asn
    2120                2125                2130

Ser Ala  Glu Leu Val Cys Leu  Thr Arg Arg Ile Leu  Leu Pro Lys
    2135                2140                2145

Asn Val  Ile Val Glu Cys Met  Val Ala Thr His His  Asn Ser Arg
    2150                2155                2160

Asn Ala  Ser Ile Trp Leu Gly  Cys Gly His Thr Asp  Arg Gly Gln
    2165                2170                2175

Leu Ser  Phe Leu Asp Leu Asn  Thr Glu Gly Tyr Thr  Ser Glu Glu
    2180                2185                2190

Val Ala  Asp Ser Arg Ile Leu  Cys Leu Ala Leu Val  His Leu Pro
    2195                2200                2205

Val Glu  Lys Glu Ser Trp Ile  Val Ser Gly Thr Gln  Ser Gly Thr
    2210                2215                2220

Leu Leu  Val Ile Asn Thr Glu  Asp Gly Lys Lys Arg  His Thr Leu
    2225                2230                2235

Glu Lys  Met Thr Asp Ser Val  Thr Cys Leu Tyr Cys  Asn Ser Phe
    2240                2245                2250

Ser Lys  Gln Ser Lys Gln Lys  Asn Phe Leu Leu Val  Gly Thr Ala
    2255                2260                2265
```

Asp Gly Lys Leu Ala Ile Phe Glu Asp Lys Thr Val Lys Leu Lys
2270 2275 2280

Gly Ala Ala Pro Leu Lys Ile Leu Asn Ile Gly Asn Val Ser Thr
2285 2290 2295

Pro Leu Met Cys Leu Ser Glu Ser Thr Asn Ser Thr Glu Arg Asn
2300 2305 2310

Val Met Trp Gly Gly Cys Gly Thr Lys Ile Phe Ser Phe Ser Asn
2315 2320 2325

Asp Phe Thr Ile Gln Lys Leu Ile Glu Thr Arg Thr Ser Gln Leu
2330 2335 2340

Phe Ser Tyr Ala Ala Phe Ser Asp Ser Asn Ile Ile Thr Val Val
2345 2350 2355

Val Asp Thr Ala Leu Tyr Ile Ala Lys Gln Asn Ser Pro Val Val
2360 2365 2370

Glu Val Trp Asp Lys Lys Thr Glu Lys Leu Cys Gly Leu Ile Asp
2375 2380 2385

Cys Val His Phe Leu Arg Glu Val Met Val Lys Glu Asn Lys Glu
2390 2395 2400

Ser Lys His Lys Met Ser Tyr Ser Gly Arg Val Lys Thr Leu Cys
2405 2410 2415

Leu Gln Lys Asn Thr Ala Leu Trp Ile Gly Thr Gly Gly Gly His
2420 2425 2430

Ile Leu Leu Leu Asp Leu Ser Thr Arg Arg Leu Ile Arg Val Ile
2435 2440 2445

Tyr Asn Phe Cys Asn Ser Val Arg Val Met Met Thr Ala Gln Leu
2450 2455 2460

Gly Ser Leu Lys Asn Val Met Leu Val Leu Gly Tyr Asn Arg Lys
2465 2470 2475

Asn Thr Glu Gly Thr Gln Lys Gln Lys Glu Ile Gln Ser Cys Leu
2480 2485 2490

Thr Val Trp Asp Ile Asn Leu Pro His Glu Val Gln Asn Leu Glu
2495 2500 2505

Lys His Ile Glu Val Arg Lys Glu Leu Ala Glu Lys Met Arg Arg
2510 2515 2520

Thr Ser Val Glu
2525

<210> SEQ ID NO 6
<211> LENGTH: 2527
<212> TYPE: PRT
<213> ORGANISM: Homo sapiens

<400> SEQUENCE: 6

Met Ala Ser Gly Ser Cys Gln Gly Cys Glu Glu Asp Glu Glu Thr Leu
1 5 10 15

Lys Lys Leu Ile Val Arg Leu Asn Asn Val Gln Glu Gly Lys Gln Ile
20 25 30

Glu Thr Leu Val Gln Ile Leu Glu Asp Leu Leu Val Phe Thr Tyr Ser
35 40 45

Glu His Ala Ser Lys Leu Phe Gln Gly Lys Asn Ile His Val Pro Leu
50 55 60

Leu Ile Val Leu Asp Ser Tyr Met Arg Val Ala Ser Val Gln Gln Val
65 70 75 80

Gly Trp Ser Leu Leu Cys Lys Leu Ile Glu Val Cys Pro Gly Thr Met

-continued

```
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
    370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510
```

-continued

```
Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925
```

-continued

```
Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                 1005

His Leu  Glu His Leu Glu Lys  Leu Glu Leu His Gln  Asn Ala Leu
    1010                 1015                 1020

Thr Ser  Phe Pro Gln Gln Leu  Cys Glu Thr Leu Lys  Ser Leu Thr
    1025                 1030                 1035

His Leu  Asp Leu His Ser Asn  Lys Phe Thr Ser Phe  Pro Ser Tyr
    1040                 1045                 1050

Leu Leu  Lys Met Ser Cys Ile  Ala Asn Leu Asp Val  Ser Arg Asn
    1055                 1060                 1065

Asp Ile  Gly Pro Ser Val Val  Leu Asp Pro Thr Val  Lys Cys Pro
    1070                 1075                 1080

Thr Leu  Lys Gln Phe Asn Leu  Ser Tyr Asn Gln Leu  Ser Phe Val
    1085                 1090                 1095

Pro Glu  Asn Leu Thr Asp Val  Val Glu Lys Leu Glu  Gln Leu Ile
    1100                 1105                 1110

Leu Glu  Gly Asn Lys Ile Ser  Gly Ile Cys Ser Pro  Leu Arg Leu
    1115                 1120                 1125

Lys Glu  Leu Lys Ile Leu Asn  Leu Ser Lys Asn His  Ile Ser Ser
    1130                 1135                 1140

Leu Ser  Glu Asn Phe Leu Glu  Ala Cys Pro Lys Val  Glu Ser Phe
    1145                 1150                 1155

Ser Ala  Arg Met Asn Phe Leu  Ala Ala Met Pro Phe  Leu Pro Pro
    1160                 1165                 1170

Ser Met  Thr Ile Leu Lys Leu  Ser Gln Asn Lys Phe  Ser Cys Ile
    1175                 1180                 1185

Pro Glu  Ala Ile Leu Asn Leu  Pro His Leu Arg Ser  Leu Asp Met
    1190                 1195                 1200

Ser Ser  Asn Asp Ile Gln Tyr  Leu Pro Gly Pro Ala  His Trp Lys
    1205                 1210                 1215

Ser Leu  Asn Leu Arg Glu Leu  Leu Phe Ser His Asn  Gln Ile Ser
    1220                 1225                 1230

Ile Leu  Asp Leu Ser Glu Lys  Ala Tyr Leu Trp Ser  Arg Val Glu
    1235                 1240                 1245

Lys Leu  His Leu Ser His Asn  Lys Leu Lys Glu Ile  Pro Pro Glu
    1250                 1255                 1260

Ile Gly  Cys Leu Glu Asn Leu  Thr Ser Leu Asp Val  Ser Tyr Asn
    1265                 1270                 1275

Leu Glu  Leu Arg Ser Phe Pro  Asn Glu Met Gly Lys  Leu Ser Lys
    1280                 1285                 1290

Ile Trp  Asp Leu Pro Leu Asp  Glu Leu His Leu Asn  Phe Asp Phe
    1295                 1300                 1305

Lys His  Ile Gly Cys Lys Ala  Lys Asp Ile Ile Arg  Phe Leu Gln
    1310                 1315                 1320

Gln Arg  Leu Lys Lys Ala Val  Pro Tyr Asn Arg Met  Lys Leu Met
```

-continued

```
    1325                1330                1335

Ile Val  Gly Asn Thr Gly Ser  Gly Lys Thr Thr Leu  Leu Gln Gln
    1340                1345                1350

Leu Met  Lys Thr Lys Lys Ser  Asp Leu Gly Met Gln  Ser Ala Thr
    1355                1360                1365

Val Gly  Ile Asp Val Lys Asp  Trp Pro Ile Gln Ile  Arg Asp Lys
    1370                1375                1380

Arg Lys  Arg Asp Leu Val Leu  Asn Val Trp Asp Phe  Ala Gly Arg
    1385                1390                1395

Glu Glu  Phe Tyr Ser Thr His  Pro His Phe Met Thr  Gln Arg Ala
    1400                1405                1410

Leu Tyr  Leu Ala Val Tyr Asp  Leu Ser Lys Gly Gln  Ala Glu Val
    1415                1420                1425

Asp Ala  Met Lys Pro Trp Leu  Phe Asn Ile Lys Ala  Arg Ala Ser
    1430                1435                1440

Ser Ser  Pro Val Ile Leu Val  Gly Thr His Leu Asp  Val Ser Asp
    1445                1450                1455

Glu Lys  Gln Arg Lys Ala Cys  Met Ser Lys Ile Thr  Lys Glu Leu
    1460                1465                1470

Leu Asn  Lys Arg Gly Phe Pro  Ala Ile Arg Asp Tyr  His Phe Val
    1475                1480                1485

Asn Ala  Thr Glu Glu Ser Asp  Ala Leu Ala Lys Leu  Arg Lys Thr
    1490                1495                1500

Ile Ile  Asn Glu Ser Leu Asn  Phe Lys Ile Arg Asp  Gln Leu Val
    1505                1510                1515

Val Gly  Gln Leu Ile Pro Asp  Cys Tyr Val Glu Leu  Glu Lys Ile
    1520                1525                1530

Ile Leu  Ser Glu Arg Lys Asn  Val Pro Ile Glu Phe  Pro Val Ile
    1535                1540                1545

Asp Arg  Lys Arg Leu Leu Gln  Leu Val Arg Glu Asn  Gln Leu Gln
    1550                1555                1560

Leu Asp  Glu Asn Glu Leu Pro  His Ala Val His Phe  Leu Asn Glu
    1565                1570                1575

Ser Gly  Val Leu Leu His Phe  Gln Asp Pro Ala Leu  Gln Leu Ser
    1580                1585                1590

Asp Leu  Tyr Phe Val Glu Pro  Lys Trp Leu Cys Lys  Ile Met Ala
    1595                1600                1605

Gln Ile  Leu Thr Val Lys Val  Glu Gly Cys Pro Lys  His Pro Lys
    1610                1615                1620

Gly Ile  Ile Ser Arg Arg Asp  Val Glu Lys Phe Leu  Ser Lys Lys
    1625                1630                1635

Arg Lys  Phe Pro Lys Asn Tyr  Met Thr Gln Tyr Phe  Lys Leu Leu
    1640                1645                1650

Glu Lys  Phe Gln Ile Ala Leu  Pro Ile Gly Glu Glu  Tyr Leu Leu
    1655                1660                1665

Val Pro  Ser Ser Leu Ser Asp  His Arg Pro Val Ile  Glu Leu Pro
    1670                1675                1680

His Cys  Glu Asn Ser Glu Ile  Ile Ile Arg Leu Tyr  Glu Met Pro
    1685                1690                1695

Tyr Phe  Pro Met Gly Phe Trp  Ser Arg Leu Ile Asn  Arg Leu Leu
    1700                1705                1710

Glu Ile  Ser Pro Tyr Met Leu  Ser Gly Arg Glu Arg  Ala Leu Arg
    1715                1720                1725
```

-continued

Pro Asn Arg Met Tyr Trp Arg Gln Gly Ile Tyr Leu Asn Trp Ser
1730 1735 1740

Pro Glu Ala Tyr Cys Leu Val Gly Ser Glu Val Leu Asp Asn His
1745 1750 1755

Pro Glu Ser Phe Leu Lys Ile Thr Val Pro Ser Cys Arg Lys Gly
1760 1765 1770

Cys Ile Leu Leu Gly Gln Val Val Asp His Ile Asp Ser Leu Met
1775 1780 1785

Glu Glu Trp Phe Pro Gly Leu Leu Glu Ile Asp Ile Cys Gly Glu
1790 1795 1800

Gly Glu Thr Leu Leu Lys Lys Trp Ala Leu Tyr Ser Phe Asn Asp
1805 1810 1815

Gly Glu Glu His Gln Lys Ile Leu Leu Asp Asp Leu Met Lys Lys
1820 1825 1830

Ala Glu Glu Gly Asp Leu Leu Val Asn Pro Asp Gln Pro Arg Leu
1835 1840 1845

Thr Ile Pro Ile Ser Gln Ile Ala Pro Asp Leu Ile Leu Ala Asp
1850 1855 1860

Leu Pro Arg Asn Ile Met Leu Asn Asn Asp Glu Leu Glu Phe Glu
1865 1870 1875

Gln Ala Pro Glu Phe Leu Leu Gly Asp Gly Ser Phe Gly Ser Val
1880 1885 1890

Tyr Arg Ala Ala Tyr Glu Gly Glu Glu Val Ala Val Lys Ile Phe
1895 1900 1905

Asn Lys His Thr Ser Leu Arg Leu Leu Arg Gln Glu Leu Val Val
1910 1915 1920

Leu Cys His Leu His His Pro Ser Leu Ile Ser Leu Leu Ala Ala
1925 1930 1935

Gly Ile Arg Pro Arg Met Leu Val Met Glu Leu Ala Ser Lys Gly
1940 1945 1950

Ser Leu Asp Arg Leu Leu Gln Gln Asp Lys Ala Ser Leu Thr Arg
1955 1960 1965

Thr Leu Gln His Arg Ile Ala Leu His Val Ala Asp Gly Leu Arg
1970 1975 1980

Tyr Leu His Ser Ala Met Ile Ile Tyr Arg Asp Leu Lys Pro His
1985 1990 1995

Asn Val Leu Leu Phe Thr Leu Tyr Pro Asn Ala Ala Ile Ile Ala
2000 2005 2010

Lys Ile Ala Asp Tyr Gly Ile Ala Gln Tyr Cys Cys Arg Met Gly
2015 2020 2025

Ile Lys Thr Ser Glu Gly Thr Pro Gly Phe Arg Ala Pro Glu Val
2030 2035 2040

Ala Arg Gly Asn Val Ile Tyr Asn Gln Gln Ala Asp Val Tyr Ser
2045 2050 2055

Phe Gly Leu Leu Leu Tyr Asp Ile Leu Thr Thr Gly Gly Arg Ile
2060 2065 2070

Val Glu Gly Leu Lys Phe Pro Asn Glu Phe Asp Glu Leu Glu Ile
2075 2080 2085

Gln Gly Lys Leu Pro Asp Pro Val Lys Glu Tyr Gly Cys Ala Pro
2090 2095 2100

Trp Pro Met Val Glu Lys Leu Ile Lys Gln Cys Leu Lys Glu Asn
2105 2110 2115

-continued

```
Pro Gln  Glu Arg Pro Thr Ser  Ala Gln Val Phe Asp  Ile Leu Asn
    2120                 2125                 2130

Ser Ala  Glu Leu Val Cys Leu  Thr Arg Arg Ile Leu  Leu Pro Lys
    2135                 2140                 2145

Asn Val  Ile Val Glu Cys Met  Val Ala Thr His His  Asn Ser Arg
    2150                 2155                 2160

Asn Ala  Ser Ile Trp Leu Gly  Cys Gly His Thr Asp  Arg Gly Gln
    2165                 2170                 2175

Leu Ser  Phe Leu Asp Leu Asn  Thr Glu Gly Tyr Thr  Ser Glu Glu
    2180                 2185                 2190

Val Ala  Asp Ser Arg Ile Leu  Cys Leu Ala Leu Val  His Leu Pro
    2195                 2200                 2205

Val Glu  Lys Glu Ser Trp Ile  Val Ser Gly Thr Gln  Ser Gly Thr
    2210                 2215                 2220

Leu Leu  Val Ile Asn Thr Glu  Asp Gly Lys Lys Arg  His Thr Leu
    2225                 2230                 2235

Glu Lys  Met Thr Asp Ser Val  Thr Cys Leu Tyr Cys  Asn Ser Phe
    2240                 2245                 2250

Ser Lys  Gln Ser Lys Gln Lys  Asn Phe Leu Leu Val  Gly Thr Ala
    2255                 2260                 2265

Asp Gly  Lys Leu Ala Ile Phe  Glu Asp Lys Thr Val  Lys Leu Lys
    2270                 2275                 2280

Gly Ala  Ala Pro Leu Lys Ile  Leu Asn Ile Gly Asn  Val Ser Thr
    2285                 2290                 2295

Pro Leu  Met Cys Leu Ser Glu  Ser Thr Asn Ser Thr  Glu Arg Asn
    2300                 2305                 2310

Val Met  Trp Gly Gly Cys Gly  Thr Lys Ile Phe Ser  Phe Ser Asn
    2315                 2320                 2325

Asp Phe  Thr Ile Gln Lys Leu  Ile Glu Thr Arg Thr  Ser Gln Leu
    2330                 2335                 2340

Phe Ser  Tyr Ala Ala Phe Ser  Asp Ser Asn Ile Ile  Thr Val Val
    2345                 2350                 2355

Val Asp  Thr Ala Leu Tyr Ile  Ala Lys Gln Asn Ser  Pro Val Val
    2360                 2365                 2370

Glu Val  Trp Asp Lys Lys Thr  Glu Lys Leu Cys Gly  Leu Ile Asp
    2375                 2380                 2385

Cys Val  His Phe Leu Arg Glu  Val Thr Val Lys Glu  Asn Lys Glu
    2390                 2395                 2400

Ser Lys  His Lys Met Ser Tyr  Ser Gly Arg Val Lys  Thr Leu Cys
    2405                 2410                 2415

Leu Gln  Lys Asn Thr Ala Leu  Trp Ile Gly Thr Gly  Gly Gly His
    2420                 2425                 2430

Ile Leu  Leu Leu Asp Leu Ser  Thr Arg Arg Leu Ile  Arg Val Ile
    2435                 2440                 2445

Tyr Asn  Phe Cys Asn Ser Val  Arg Val Met Met Thr  Ala Gln Leu
    2450                 2455                 2460

Gly Ser  Leu Lys Asn Val Met  Leu Val Leu Gly Tyr  Asn Arg Lys
    2465                 2470                 2475

Asn Thr  Glu Gly Thr Gln Lys  Gln Lys Glu Ile Gln  Ser Cys Leu
    2480                 2485                 2490

Thr Val  Trp Asp Ile Asn Leu  Pro His Glu Val Gln  Asn Leu Glu
    2495                 2500                 2505

Lys His  Ile Glu Val Arg Lys  Glu Leu Ala Glu Lys  Met Arg Arg
```

-continued

```
    2510                2515                2520

Thr Ser  Val Glu
    2525


<210> SEQ ID NO 7
<211> LENGTH: 2527
<212> TYPE: PRT
<213> ORGANISM: Homo sapiens

<400> SEQUENCE: 7

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Ser Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350
```

-continued

```
Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
    370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
```

-continued

```
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
    1175                1180                1185
```

-continued

```
Pro Glu  Ala Ile Leu Asn Leu  Pro His Leu Arg Ser  Leu Asp Met
    1190                 1195                 1200

Ser Ser  Asn Asp Ile Gln Tyr  Leu Pro Gly Pro Ala  His Trp Lys
    1205                 1210                 1215

Ser Leu  Asn Leu Arg Glu Leu  Leu Phe Ser His Asn  Gln Ile Ser
    1220                 1225                 1230

Ile Leu  Asp Leu Ser Glu Lys  Ala Tyr Leu Trp Ser  Arg Val Glu
    1235                 1240                 1245

Lys Leu  His Leu Ser His Asn  Lys Leu Lys Glu Ile  Pro Pro Glu
    1250                 1255                 1260

Ile Gly  Cys Leu Glu Asn Leu  Thr Ser Leu Asp Val  Ser Tyr Asn
    1265                 1270                 1275

Leu Glu  Leu Arg Ser Phe Pro  Asn Glu Met Gly Lys  Leu Ser Lys
    1280                 1285                 1290

Ile Trp  Asp Leu Pro Leu Asp  Glu Leu His Leu Asn  Phe Asp Phe
    1295                 1300                 1305

Lys His  Ile Gly Cys Lys Ala  Lys Asp Ile Ile Arg  Phe Leu Gln
    1310                 1315                 1320

Gln Arg  Leu Lys Lys Ala Val  Pro Tyr Asn Arg Met  Lys Leu Met
    1325                 1330                 1335

Ile Val  Gly Asn Thr Gly Ser  Gly Lys Thr Thr Leu  Leu Gln Gln
    1340                 1345                 1350

Leu Met  Lys Thr Lys Lys Ser  Asp Leu Gly Met Gln  Ser Ala Thr
    1355                 1360                 1365

Val Gly  Ile Asp Val Lys Asp  Trp Pro Ile Gln Ile  Arg Asp Lys
    1370                 1375                 1380

Arg Lys  Arg Asp Leu Val Leu  Asn Val Trp Asp Phe  Ala Gly Arg
    1385                 1390                 1395

Glu Glu  Phe Tyr Ser Thr His  Pro His Phe Met Thr  Gln Arg Ala
    1400                 1405                 1410

Leu Tyr  Leu Ala Val Tyr Asp  Leu Ser Lys Gly Gln  Ala Glu Val
    1415                 1420                 1425

Asp Ala  Met Lys Pro Trp Leu  Phe Asn Ile Lys Ala  Arg Ala Ser
    1430                 1435                 1440

Ser Ser  Pro Val Ile Leu Val  Gly Thr His Leu Asp  Val Ser Asp
    1445                 1450                 1455

Glu Lys  Gln Arg Lys Ala Cys  Met Ser Lys Ile Thr  Lys Glu Leu
    1460                 1465                 1470

Leu Asn  Lys Arg Gly Phe Pro  Ala Ile Arg Asp Tyr  His Phe Val
    1475                 1480                 1485

Asn Ala  Thr Glu Glu Ser Asp  Ala Leu Ala Lys Leu  Arg Lys Thr
    1490                 1495                 1500

Ile Ile  Asn Glu Ser Leu Asn  Phe Lys Ile Arg Asp  Gln Leu Val
    1505                 1510                 1515

Val Gly  Gln Leu Ile Pro Asp  Cys Tyr Val Glu Leu  Glu Lys Ile
    1520                 1525                 1530

Ile Leu  Ser Glu Arg Lys Asn  Val Pro Ile Glu Phe  Pro Val Ile
    1535                 1540                 1545

Asp Arg  Lys Arg Leu Leu Gln  Leu Val Arg Glu Asn  Gln Leu Gln
    1550                 1555                 1560

Leu Asp  Glu Asn Glu Leu Pro  His Ala Val His Phe  Leu Asn Glu
    1565                 1570                 1575
```

```
Ser Gly  Val Leu Leu His Phe  Gln Asp Pro Ala Leu  Gln Leu Ser
    1580                 1585                 1590

Asp Leu  Tyr Phe Val Glu Pro  Lys Trp Leu Cys Lys  Ile Met Ala
    1595                 1600                 1605

Gln Ile  Leu Thr Val Lys Val  Glu Gly Cys Pro Lys  His Pro Lys
    1610                 1615                 1620

Gly Ile  Ile Ser Arg Arg Asp  Val Glu Lys Phe Leu  Ser Lys Lys
    1625                 1630                 1635

Arg Lys  Phe Pro Lys Asn Tyr  Met Ser Gln Tyr Phe  Lys Leu Leu
    1640                 1645                 1650

Glu Lys  Phe Gln Ile Ala Leu  Pro Ile Gly Glu Glu  Tyr Leu Leu
    1655                 1660                 1665

Val Pro  Ser Ser Leu Ser Asp  His Arg Pro Val Ile  Glu Leu Pro
    1670                 1675                 1680

His Cys  Glu Asn Ser Glu Ile  Ile Ile Arg Leu Tyr  Glu Met Pro
    1685                 1690                 1695

Tyr Phe  Pro Met Gly Phe Trp  Ser Arg Leu Ile Asn  Arg Leu Leu
    1700                 1705                 1710

Glu Ile  Ser Pro Tyr Met Leu  Ser Gly Arg Glu Arg  Ala Leu Arg
    1715                 1720                 1725

Pro Asn  Arg Met Tyr Trp Arg  Gln Gly Ile Tyr Leu  Asn Trp Ser
    1730                 1735                 1740

Pro Glu  Ala Tyr Cys Leu Val  Gly Ser Glu Val Leu  Asp Asn His
    1745                 1750                 1755

Pro Glu  Ser Phe Leu Lys Ile  Thr Val Pro Ser Cys  Arg Lys Gly
    1760                 1765                 1770

Cys Ile  Leu Leu Gly Gln Val  Val Asp His Ile Asp  Ser Leu Met
    1775                 1780                 1785

Glu Glu  Trp Phe Pro Gly Leu  Leu Glu Ile Asp Ile  Cys Gly Glu
    1790                 1795                 1800

Gly Glu  Thr Leu Leu Lys Lys  Trp Ala Leu Tyr Ser  Phe Asn Asp
    1805                 1810                 1815

Gly Glu  Glu His Gln Lys Ile  Leu Leu Asp Asp Leu  Met Lys Lys
    1820                 1825                 1830

Ala Glu  Glu Gly Asp Leu Leu  Val Asn Pro Asp Gln  Pro Arg Leu
    1835                 1840                 1845

Thr Ile  Pro Ile Ser Gln Ile  Ala Pro Asp Leu Ile  Leu Ala Asp
    1850                 1855                 1860

Leu Pro  Arg Asn Ile Met Leu  Asn Asn Asp Glu Leu  Glu Phe Glu
    1865                 1870                 1875

Gln Ala  Pro Glu Phe Leu Leu  Gly Asp Gly Ser Phe  Gly Ser Val
    1880                 1885                 1890

Tyr Arg  Ala Ala Tyr Glu Gly  Glu Glu Val Ala Val  Lys Ile Phe
    1895                 1900                 1905

Asn Lys  His Thr Ser Leu Arg  Leu Leu Arg Gln Glu  Leu Val Val
    1910                 1915                 1920

Leu Cys  His Leu His His Pro  Ser Leu Ile Ser Leu  Leu Ala Ala
    1925                 1930                 1935

Gly Ile  Arg Pro Arg Met Leu  Val Met Glu Leu Ala  Ser Lys Gly
    1940                 1945                 1950

Ser Leu  Asp Arg Leu Leu Gln  Gln Asp Lys Ala Ser  Leu Thr Arg
    1955                 1960                 1965

Thr Leu  Gln His Arg Ile Ala  Leu His Val Ala Asp  Gly Leu Arg
```

```
    1970                1975                1980

Tyr Leu  His Ser Ala Met Ile  Ile Tyr Arg Asp Leu  Lys Pro His
    1985                1990                1995

Asn Val  Leu Leu Phe Thr Leu  Tyr Pro Asn Ala Ala  Ile Ile Ala
    2000                2005                2010

Lys Ile  Ala Asp Tyr Gly Ile  Ala Gln Tyr Cys Cys  Arg Met Gly
    2015                2020                2025

Ile Lys  Thr Ser Glu Gly Thr  Pro Gly Phe Arg Ala  Pro Glu Val
    2030                2035                2040

Ala Arg  Gly Asn Val Ile Tyr  Asn Gln Gln Ala Asp  Val Tyr Ser
    2045                2050                2055

Phe Gly  Leu Leu Leu Tyr Asp  Ile Leu Thr Thr Gly  Gly Arg Ile
    2060                2065                2070

Val Glu  Gly Leu Lys Phe Pro  Asn Glu Phe Asp Glu  Leu Glu Ile
    2075                2080                2085

Gln Gly  Lys Leu Pro Asp Pro  Val Lys Glu Tyr Gly  Cys Ala Pro
    2090                2095                2100

Trp Pro  Met Val Glu Lys Leu  Ile Lys Gln Cys Leu  Lys Glu Asn
    2105                2110                2115

Pro Gln  Glu Arg Pro Thr Ser  Ala Gln Val Phe Asp  Ile Leu Asn
    2120                2125                2130

Ser Ala  Glu Leu Val Cys Leu  Thr Arg Arg Ile Leu  Leu Pro Lys
    2135                2140                2145

Asn Val  Ile Val Glu Cys Met  Val Ala Thr His His  Asn Ser Arg
    2150                2155                2160

Asn Ala  Ser Ile Trp Leu Gly  Cys Gly His Thr Asp  Arg Gly Gln
    2165                2170                2175

Leu Ser  Phe Leu Asp Leu Asn  Thr Glu Gly Tyr Thr  Ser Glu Glu
    2180                2185                2190

Val Ala  Asp Ser Arg Ile Leu  Cys Leu Ala Leu Val  His Leu Pro
    2195                2200                2205

Val Glu  Lys Glu Ser Trp Ile  Val Ser Gly Thr Gln  Ser Gly Thr
    2210                2215                2220

Leu Leu  Val Ile Asn Thr Glu  Asp Gly Lys Lys Arg  His Thr Leu
    2225                2230                2235

Glu Lys  Met Thr Asp Ser Val  Thr Cys Leu Tyr Cys  Asn Ser Phe
    2240                2245                2250

Ser Lys  Gln Ser Lys Gln Lys  Asn Phe Leu Leu Val  Gly Thr Ala
    2255                2260                2265

Asp Gly  Lys Leu Ala Ile Phe  Glu Asp Lys Thr Val  Lys Leu Lys
    2270                2275                2280

Gly Ala  Ala Pro Leu Lys Ile  Leu Asn Ile Gly Asn  Val Ser Thr
    2285                2290                2295

Pro Leu  Met Cys Leu Ser Glu  Ser Thr Asn Ser Thr  Glu Arg Asn
    2300                2305                2310

Val Met  Trp Gly Gly Cys Gly  Thr Lys Ile Phe Ser  Phe Ser Asn
    2315                2320                2325

Asp Phe  Thr Ile Gln Lys Leu  Ile Glu Thr Arg Thr  Ser Gln Leu
    2330                2335                2340

Phe Ser  Tyr Ala Ala Phe Ser  Asp Ser Asn Ile Ile  Thr Val Val
    2345                2350                2355

Val Asp  Thr Ala Leu Tyr Ile  Ala Lys Gln Asn Ser  Pro Val Val
    2360                2365                2370
```

-continued

```
Glu Val  Trp Asp Lys Lys Thr  Glu Lys Leu Cys Gly  Leu Ile Asp
    2375                 2380                 2385

Cys Val  His Phe Leu Arg Glu  Val Met Val Lys Glu  Asn Lys Glu
    2390                 2395                 2400

Ser Lys  His Lys Met Ser Tyr  Ser Gly Arg Val Lys  Thr Leu Cys
    2405                 2410                 2415

Leu Gln  Lys Asn Thr Ala Leu  Trp Ile Gly Thr Gly  Gly Gly His
    2420                 2425                 2430

Ile Leu  Leu Leu Asp Leu Ser  Thr Arg Arg Leu Ile  Arg Val Ile
    2435                 2440                 2445

Tyr Asn  Phe Cys Asn Ser Val  Arg Val Met Met Thr  Ala Gln Leu
    2450                 2455                 2460

Gly Ser  Leu Lys Asn Val Met  Leu Val Leu Gly Tyr  Asn Arg Lys
    2465                 2470                 2475

Asn Thr  Glu Gly Thr Gln Lys  Gln Lys Glu Ile Gln  Ser Cys Leu
    2480                 2485                 2490

Thr Val  Trp Asp Ile Asn Leu  Pro His Glu Val Gln  Asn Leu Glu
    2495                 2500                 2505

Lys His  Ile Glu Val Arg Lys  Glu Leu Ala Glu Lys  Met Arg Arg
    2510                 2515                 2520

Thr Ser  Val Glu
    2525
```